(12) United States Patent
Krämer et al.

(10) Patent No.: US 6,211,214 B1
(45) Date of Patent: Apr. 3, 2001

(54) BIPHENYL ETHER OXAZOLINES AND THEIR USE AS PEST-CONTROL AGENTS

(75) Inventors: Wolfgang Krämer, Burscheid; Udo Kraatz, Leverkusen; Christoph Erdelen, Leichlingen; Ulrike Wachendorff-Neumann, Neuwied; Andreas Turberg, Haan; Norbert Mencke, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/068,819

(22) PCT Filed: Nov. 6, 1996

(86) PCT No.: PCT/EP96/04846

§ 371 Date: May 12, 1998

§ 102(e) Date: May 12, 1998

(87) PCT Pub. No.: WO97/19067

PCT Pub. Date: May 29, 1997

(30) Foreign Application Priority Data

Nov. 17, 1995 (DE) ................................. 195 42 934
Sep. 18, 1996 (DE) ................................. 196 38 047

(51) Int. Cl.[7] ............... C07D 263/14; C07D 413/12; A01N 43/76

(52) U.S. Cl. ............ 514/374; 514/212; 514/229.2; 514/236.8; 514/326; 514/340; 514/365; 540/603; 544/65; 544/137; 546/208; 546/271.4; 548/146; 548/237

(58) Field of Search ................ 514/212, 229.2, 514/236.8, 326, 340, 365, 374; 540/603; 544/65, 137; 546/208, 271.4; 548/146, 237

(56) References Cited

U.S. PATENT DOCUMENTS 5,141,948  8/1992  Miyamoto et al. ............... 514/365
5,354,905  10/1994  Sato et al. ....................... 564/186
5,807,877 * 9/1998  Lantzsh ........................... 514/374
5,969,147 * 10/1999  Lantzsch et al. ................ 548/237

FOREIGN PATENT DOCUMENTS 0 432 661 * 6/1991 (EP) .
0 639 572 * 2/1995 (EP) .
0 696 584 * 2/1996 (EP) .
WO 96/11190 * 4/1996 (WO) .
WO 96/22283 * 7/1996 (WO) .

OTHER PUBLICATIONS

Bach et al., Nonsteroidal Hypocholesteremic Agents, Journal of Medicinal Chemistry, vol. 11, No. 5, pp. 987–993, Sep. 1968.*

* cited by examiner

Primary Examiner—Mukund J. Shah
Assistant Examiner—Brenda Coleman
(74) Attorney, Agent, or Firm—Norris McLaughlin & Marcus P.A.

(57) ABSTRACT

The present invention relates to novel biphenyl ether-oxazolines of the formula (I)

(I)

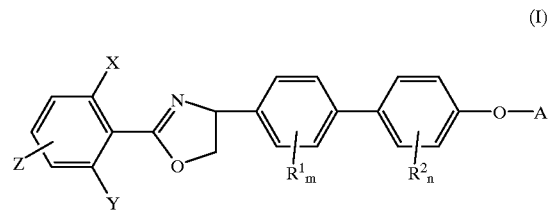

in which
X, Y, Z, $R^1$, $R^2$, A, m and n have the meaning given in the description,
to processes for their preparation and to their use for controlling animal pests, and two novel intermediate products.

10 Claims, No Drawings

BIPHENYL ETHER OXAZOLINES AND THEIR USE AS PEST-CONTROL AGENTS

This application is the national stage of PCT/EP96/04846, filed Nov. 6, 1996.

The present invention relates to novel biphenyl ether-oxazolines, processes for their preparation and their use for controlling animal pests, and to novel intermediate products.

It is already known that certain substituted biphenyl-oxazolines, such as, for example, 2-(2,6-difluorophenyl)-4-(4'-methoxybiphenyl-4-yl)-1,3-oxazoline, have an insecticidal and acaricidal action (cf. EP-A 0 432 661).

However, the level of action and/or duration of action of these known compounds is not completely satisfactory in all fields of use, especially against certain organisms or if low concentrations are used.

Novel biphenyl ether-oxazolines of the formula (I)

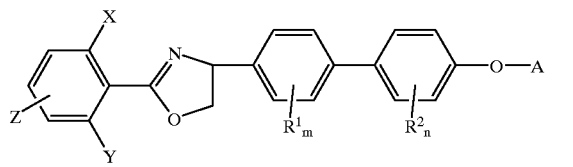

(I)

in which

X represents hydrogen, fluorine or chlorine,

Y represents fluorine, chlorine or methyl,

Z represents hydrogen, halogen, alkyl, alkoxy or dialkylamino, $R^1$ and $R^2$ independently of one another represent halogen, alkyl, alkoxy, alkylthio, halogenoalkyl, halogenoalkoxy or halogenoalkylthio, m and n independently of one another represent 0, 1 or 2 and A represents the grouping —(CH$_2$)$_p$—(CR$^3$R$^4$)$_q$—(CH$_2$)$_r$—R wherein $R^3$ and $R^4$ independently of one another represent hydrogen or alkyl, p, q and r independently of one another represent 0, 1, 2 or 3, at least one index being other than 0, and R represents cyano; or represents an optionally substituted, saturated, partly saturated or unsaturated 5- or 6-membered heterocyclic radical, or represents one of the following groupings:

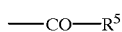
(a)

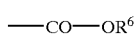
(b)

(c)

(d)

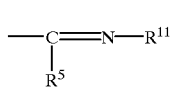
(e)

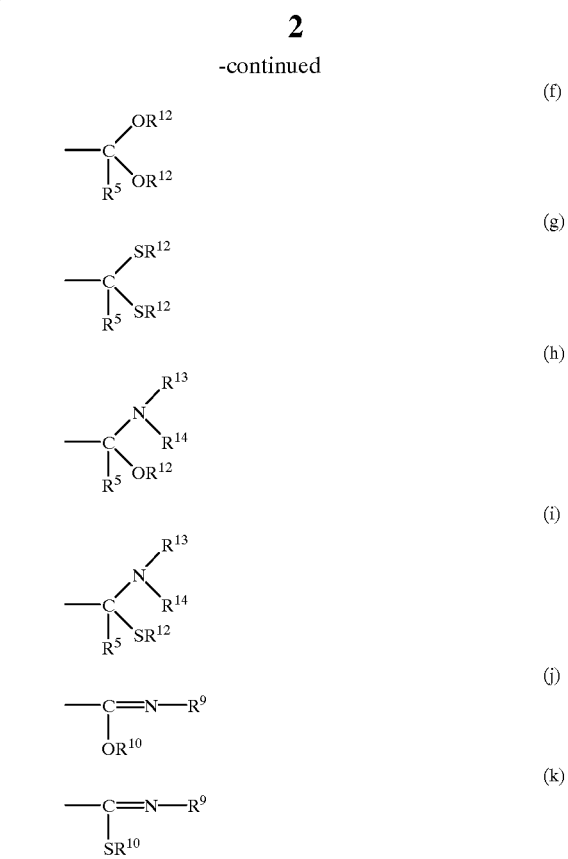

wherein $R^5$ represents hydrogen, alkyl, halogenoalkyl, alkenyl, halogenoalkenyl, optionally substituted cycloalkyl or optionally substituted aryl, $R^6$ represents hydrogen, alkyl, alkenyl, halogenoalkyl, halogenoalkenyl, optionally substituted arylalkyl or in each case optionally substituted cycloalkyl or cycloalkylalkyl, $R^7$ and $R^8$ independently of one another represent hydrogen, alkyl, alkoxy, alkenyl, halogenoalkyl, halogenoalkenyl, in each case optionally substituted aryl or arylalkyl, or in each case optionally substituted cycloalkyl or cycloalkylalkyl, or represent —OR$^6$ or —NR$^5$R$^6$, wherein $R^5$ and $R^6$ have the abovementioned meaning, or $R^7$ and $R^8$ together represent a 5- or 6-membered alkylene chain, which optionally contains an oxygen atom, $R^9$ and $R^{10}$ independently of one another represent alkyl, $R^{11}$ represents —OR$^6$, —NR$^5$R$^6$ or —N(R$^5$)—COOR$^6$, wherein $R^5$ and $R^6$ have the abovementioned meaning, and $R^{12}$, $R^{13}$ and $R^{14}$ independently of one another represent alkyl, have now been found.

The biphenyl ether-oxazolines of the formula (I) can be obtained as optical and/or geometric isomers, also depending on the substituents. The present invention relates both to the isomer mixtures and to the pure isomers.

It has furthermore been found that the biphenyl ether-oxazolines of the formula (I) are obtained by a process in which hydroxybiphenyloxazolines of the formula (II)

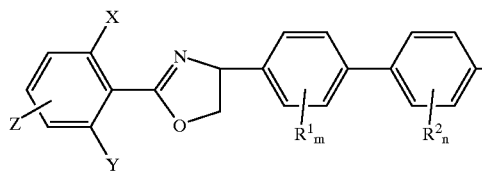

(II)

in which

X, Y, Z, R$^1$, R$^2$, m and n have the abovementioned meaning, are reacted with a compound of the formula (III)

M—A     (III)

in which

A has the abovementioned meaning and

M represents a leaving group, if appropriate in the presence of a base and/or a catalyst and if appropriate in the presence of a diluent.

It has furthermore been found that the novel substituted biphenyl ether-oxazolines of the formula (I) are particularly suitable for controlling animal pests, in particular insects, arachnids and nematodes which occur in agriculture, in forestry, in the preservation of stored products and materials and in the hygiene sector.

Formula (I) provides a general definition of the compounds according to the invention.

Preferred substituents and ranges of the radicals listed in the formulae mentioned above and below are explained in the following.

X preferably represents hydrogen, fluorine or chlorine.

Y preferably represents fluorine, chlorine or methyl.

Z preferably represents hydrogen, fluorine, chlorine, $C_1$–$C_4$-alkyl, $C_1$–$C_4$-alkoxy or di($C_1$–$C_4$)alkylamino.

R$^1$ and R$^2$ independently of one another preferably represent fluorine, chlorine, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or $C_1$–$C_4$-halogenoalkylthio.

m and n independently of one another preferably represent 0, 1 or 2.

A preferably represents the grouping $(CH_2)_p$—$(CR^3R^4)_q$—$(CH_2)_r$—R, wherein R$^3$ and R$^4$ independently of one another represent hydrogen or $C_1$–$C_4$-alkyl, p, q and r independently of one another represent 0, 1, 2 or 3, at least one index being other than 0 and the sum of the indices being not greater than 5.

R Preferably represents cyano; or represents a saturated, partly saturated or unsaturated 5- or 6-membered heterocyclic radical which has 1 to 3 identical or different heteroatoms from the series consisting of nitrogen, oxygen and sulfur and is optionally substituted by halogen, $C_1$–$C_4$-alkyl or $C_1$–$C_4$-halogenoalkyl, or represents one of the following groupings:

—CO—R$^5$     (a)

—CO—OR$^6$     (b)

—CO—NR$^7$R$^8$     (c)

—CS—NR$^7$R$^8$     (d)

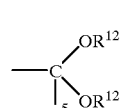 (e)

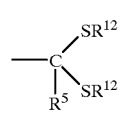 (f)

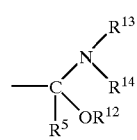 (g)

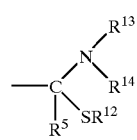 (h)

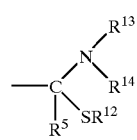 (i)

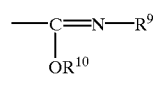 (j)

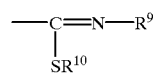 (k)

wherein

R$^5$ represents hydrogen, $C_1$–$C_6$-alkyl, $C_1$–$C_4$-halogenoalkyl, $C_2$–$C_6$-alkenyl or $C_2$–$C_6$-halogenoalkyl; or $C_3$–$C_6$-cycloalkyl which is optionally substituted once or several times in an identical or different manner by $C_1$–$C_4$-alkyl, halogen or $C_1$–$C_4$-halogenoalkyl, or represents phenyl which is optionally substituted once to five times in an identical or different manner by halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, di($C_1$–$C_4$)alkylamino, $C_1$–$C_4$-alkylcarbonylamino, $C_1$–$C_4$-alkylcarbonyl-$C_1$–$C_4$-alkyl amino, cyano, nitro, —COOR$^{15}$ or —CONR$^{16}$R$^{17}$, R$^6$ represents hydrogen, $C_1$–$C_6$-alkyl, $C_1$–$C_6$-halogenoalkyl, $C_2$–$C_6$-alkenyl or $C_2$–$C_6$-halogenoalkenyl; or $C_3$–$C_6$-cycloalkyl or $C_3$–$C_6$-cycloalkyl-$C_1$–$C_4$-alkyl, in each case optionally substituted once or several times in an identical or different manner by $C_1$–$C_4$-alkyl, halogen or $C_1$–$C_4$-halogenoalkyl, or represents $C_6$–$C_{10}$-aryl-$C_1$–$C_6$-alkyl which is optionally substituted once to five times in an identical or different manner by halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$- halogenoalkylthio, di(C₁–C₄)alkylamino, cyano, nitro, —COOR¹⁵ or —CONR¹⁶R¹⁷,

R⁷ and R⁸ independently of one another represent hydrogen, C₁–C₄-alkyl, C₁–C₄-alkoxy, C₁–C₄-halogenoalkyl, C₂–C₆-alkenyl or C₂–C₆-halogenoalkenyl; or C₃–C₆-cycloalkyl or C₃–C₆-cycloalkyl-C₁–C₄-alkyl, in each case optionally substituted once or several times in an identical or different manner by C₁–C₄-alkyl, halogen or C₁–C₄-halogenoalkyl, or represent phenyl or phenyl-C₁–C₄-alkyl, in each case optionally substituted once to five times in an identical or different manner by halogen, C₁–C₄-alkyl, C₁–C₄-alkoxy, C₁–C₄-alkylthio, C₁–C₄-halogenoalkyl, C₁–C₄-halogenoalkoxy, C₁–C₄-halogenoalkylthio, di(C₁–C₄)alkylamino, cyano, nitro, —COOR¹⁵ or —CONR¹⁶R¹⁷, or represent —OR⁶ or —NR⁵R⁶, or R⁷ and R⁸ together represent —(CH₂)₅—, —(CH₂)₆— or —(CH₂)₂—O—(CH₂)₂—;

R⁹ and R¹⁰ independently of one another represent C₁–C₄-alkyl;

R¹¹ represents —OR⁶—, —NR⁵R⁶ or —N(R⁵)—COOR⁶, and

R¹², R¹³ and R¹⁴ independently of one another represent C₁–C₄-alkyl.

R¹⁵ preferably represents hydrogen, C₁–C₄-alkyl or C₁–C₄-halogenoalkyl; or C₃–C₆-cycloalkyl which is optionally substituted once or several times in an identical or different manner by C₁–C₄-alkyl, halogen or C₁–C₄-halogenoalkyl, or represents phenyl which is optionally substituted once to five times in an identical or different manner by halogen, C₁–C₄-alkyl, C₁–C₄-alkoxy, C₁–C₄-alkylthio, C₁–C₄-halogenoalkyl, C₁–C₄-halogenoalkoxy, C₁–C₄-halogenoalkylthio, di(C₁–C₄)alkylamino, cyano, nitro, C₁–C₆-alkoxycarbonyl or di(C₁–C₆)alkylaminocarbonyl.

R¹⁶ and R¹⁷ independently of one another preferably represent hydrogen, C₁–C₄-alkyl, C₁–C₄-alkoxy, C₁–C₄-halogenoalkyl, C₂–C₆-alkenyl or C₂–C₆-halogenoalkenyl; or C₃–C₆-cycloalkyl or C₃–C₆-cycloalkyl-C₁–C₄-alkyl, in each case optionally substituted once or several times in an identical or different manner by C₁–C₄-alkyl, halogen or C₁–C₄-halogenoalkyl, or represent phenyl or phenyl-C₁–C₄-alkyl, in each case optionally substituted once to five times in an identical or different manner by halogen, C₁–C₄-alkyl, C₁–C₄-alkoxy, C₁–C₄-alkylthio, C₁–C₄-halogenoalkyl, C₁–C₄-halogenoalkoxy, C₁–C₄-halogenoalkylthio, di(C₁–C₄)alkylamino, cyano, nitro, C₁–C₆-alkoxycarbonyl or di(C₁–C₆)alkylaminocarbonyl, or represent —OR⁶ or —NR⁵R⁶, or R¹⁶ and R¹⁷ together represent —(CH₂)₅—, —(CH₂)₆— or —(CH₂)₂—O—(CH₂)₂.

X particularly preferably represents hydrogen, fluorine or chlorine.

Y particularly preferably represents fluorine or chlorine.

Z particularly preferably represents hydrogen, fluorine, chlorine, methyl, ethyl, methoxy, dimethylamino or diethylamino.

R¹ and R² independently of one another particularly preferably represent fluorine, chlorine, methyl, ethyl, methoxy, methylthio, trifluoromethyl, trifluoromethoxy or trifluoromethylthio.

m and n independently of one another particularly preferably represent 0, 1 or 2.

A particularly preferably represents the grouping (CH₂)ₚ—(CR³R⁴)_q—(CH₂)ᵣ—R, wherein R³ and R⁴ independently of one another represent hydrogen, methyl, ethyl, n- or i-propyl, n-, i-, s- or t-butyl;

p, q and r independently of one another represent 0, 1, 2 or 3, at least one index being other than 0 and the sum of the indices being not greater than 5, in particular not greater than 3.

R particularly preferably represents cyano; or represents one of the following heterocyclic radicals

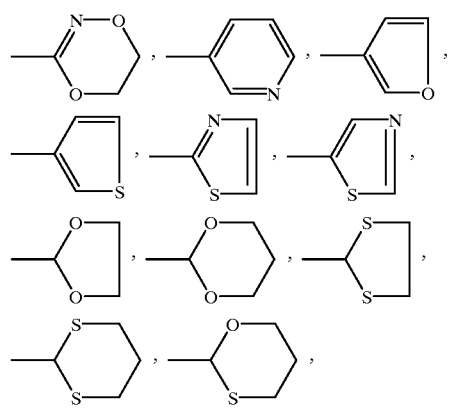

which are optionally substituted once to three times in an identical or different manner by fluorine, chlorine, bromine, methyl, ethyl, n- or i-propyl or trifluoromethyl;

or represents one of the following groupings:

   (a)

   (b)

   (c)

   (d)

   (e)

   (f)

   (g)

   (h)

-continued

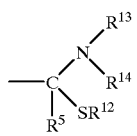
(i)

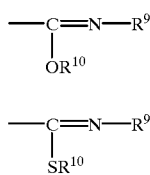
(j)

(k)

wherein

R⁵ represents hydrogen; methyl, ethyl, n- or i-propyl, the isomeric butyls, the isomeric pentyls or the isomeric hexyls; or $C_1$–$C_2$-halogenoalkyl having 1 to 5 identical or different halogen atoms, such as F and Cl atoms, $C_3$–$C_6$-alkenyl or $C_3$–$C_6$-halogenoalkenyl having 1 to 5 identical or different halogen atoms, such as F and Cl atoms; or cyclopropyl, cyclopentyl or cyclohexyl, in each case optionally substituted once to three times in an identical or different manner by fluorine, chlorine, methyl, ethyl, n- or i-propyl or $C_1$–$C_2$-halogenoalkyl having 1 to 5 identical or different halogen atoms, such as F and Cl atoms, or represents phenyl which is optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, methylcarbonylamino, ethylcarbonylamino, methylcarbonyl-methylamino, cyano, nitro, —$COOR^{15}$ or —$CONR^{16}R^{17}$, R⁶ represents hydrogen, methyl, ethyl, n- or i-propyl or n-, i-, s- or t-butyl; or $C_1$–$C_2$-halogenoalkyl having 1 to 5 identical or different halogen atoms, such as F and Cl atoms; or allyl which is optionally substituted once or several times by fluorine and/or chlorine; or cyclopropyl, cyclopentyl, cyclohexyl, cyclopropyl-$C_1$–$C_2$-alkyl, cyclopentyl-$C_1$–$C_2$-alkyl or cyclohexyl-$C_1$–$C_2$-alkyl, in each case optionally substituted once to three times in an identical or different manner by fluorine, chlorine, methyl, ethyl, n- or i-propyl or $C_1$–$C_2$-halogenoalkyl having 1 to 5 identical or different halogen atoms, such as F and Cl atoms, or represents phenyl-$C_1$–$C_2$-alkyl or naphthyl-$C_1$–$C_2$-alkyl, in each case optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, cyano, nitro, —$COOR^{15}$ or —$CONR^{16}R^{17}$, R⁷ and R⁸ independently of one another represent hydrogen, $C_1$–$C_4$-alkyl, methoxy, ethoxy or $C_1$–$C_3$-halogenoalkyl having 1 to 5 identical or different halogen atoms, such as F and Cl atoms; or allyl which is optionally substituted once or several times by fluorine and/or chlorine; or cyclopropyl, cyclopentyl, cyclohexyl, cyclopropylmethyl, cyclopentylmethyl or cyclohexylmethyl, in each case optionally substituted once to three times in an identical or different manner by fluorine, chlorine, methyl, ethyl, n- or i-propyl or trifluoromethyl, or represent phenyl or phenyl-$C_1$–$C_2$-alkyl, in each case optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, cyano, nitro, —$COOR^{15}$ or —$CONR^{16}R^{17}$, or represent —$OR^6$ or —$NR^5R^6$, R⁹ and R¹⁰ independently of one another represent methyl, ethyl or n- or i-propyl;

R¹¹ represents —$OR^6$, —$NR^5R^6$ or —$N(R^5)$—$COOR^6$, and

R¹², R¹³ and R¹⁴ independently of one another represent methyl, ethyl or n- or i-propyl.

R¹⁵ particularly preferably represents hydrogen, methyl, ethyl, or n- or i-propyl; or $C_1$–$C_2$-halogenoalkyl having 1 to 5 identical or different halogen atoms, such as F and Cl atoms; or cyclopropyl, cyclopentyl or cyclohexyl, in each case optionally substituted once to three times in an identical or different manner by fluorine, chlorine, methyl, ethyl, n- or i-propyl or $C_1$–$C_2$-halogenoalkyl having 1 to 5 identical or different halogen atoms, such as F and Cl atoms, or represents phenyl which is optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, cyano, nitro, $C_1$–$C_4$-alkoxycarbonyl or di($C_1$–$C_4$)alkylaminocarbonyl.

R¹⁶ and R¹⁷ independently of one another particularly preferably represent hydrogen, $C_1$–$C_4$-alkyl, methoxy, ethoxy or $C_1$–$C_3$-halogenoalkyl having 1 to 5 identical or different halogen atoms, such as F and Cl atoms; or allyl which is optionally substituted once or several times by fluorine and/or chlorine; or cyclopropyl, cyclopentyl, cyclohexyl, cyclopropylmethyl, cyclopentylmethyl or cyclohexylmethyl, in each case optionally substituted once to three times in an identical or different manner by fluorine, chlorine, methyl, ethyl, n- or i-propyl or trifluoromethyl, or represent phenyl or phenyl-$C_1$–$C_2$-alkyl, in each case optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, cyano, nitro, $C_1$–$C_4$-alkoxycarbonyl or di($C_1$–$C_4$)alkylaminocarbonyl, or represent —$OR^6$ or —$NR^5R^6$.

In each case, if m=2 and/or n=2, the substituents R¹ and R² can be identical or different.

The radical definitions and explanations listed above generally or listed in preferred ranges apply accordingly to the end products and to the starting substances and intermediate products. These definitions of radicals can be combined as desired with one another, that is to say also between the particularly preferred ranges.

The compounds of the general formula (I) in which a combination of the meanings listed above as preferred (preferably) is present are preferred according to the invention.

The compounds of the general formula (I) in which a combination of the meanings listed above as particularly preferred is present are particularly preferred according to the invention.

In the radical definitions listed above and below, hydrocarbon radicals, such as alkyl or alkenyl—including in combinations with heteroatoms, such as alkoxy or alkylthio—are, where possible, in each case straight-chain or branched.

Preferred compounds according to the invention are substances of the formulae (Ia) to (Ie):

(Ia)
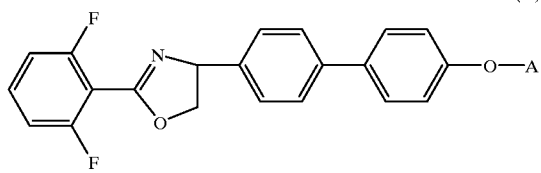

(Ib)
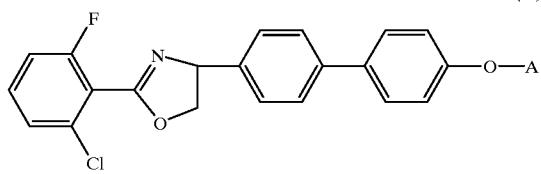

(Ic)
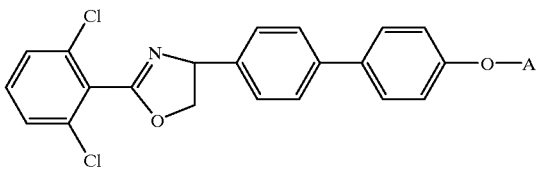

(Id)
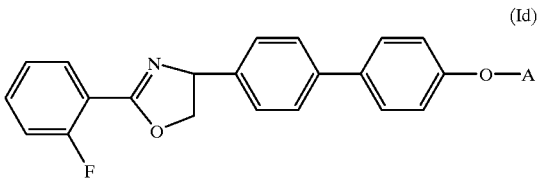

(Ie)
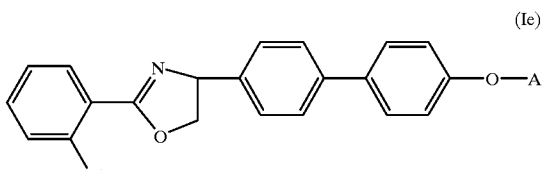

in which

A has the meanings given in the definition of the invention.

Preferred compounds according to the invention are also substances of the formula (IA):

(IA)
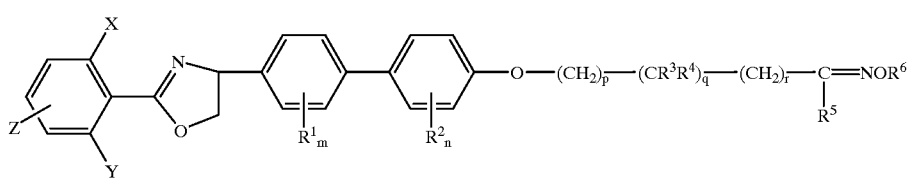

in which $R^1$, $R^2$, $R^3$, $R^4$, $R^5$, $R^6$, X, Y, Z, m, n, p, q and r have the meanings given in the definition of the invention, and among these, in turn, those where m=0 and Z=hydrogen are preferred, particularly preferred m=0, n=0 and Z=hydrogen.

If 2-(2,6-difluorophenyl)-4-(4'-hydroxybiphenyl-4-yl)-1,3-oxazoline and benzoylmethyl bromide are used as starting substances for carrying out the process according to the invention, the course of the reaction can be represented by the following equation:

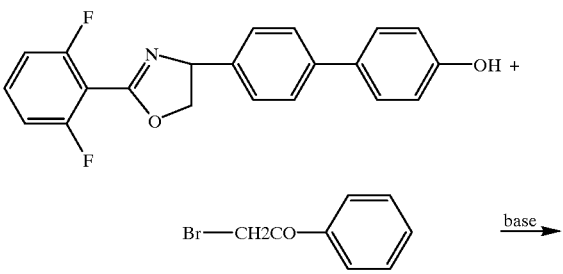

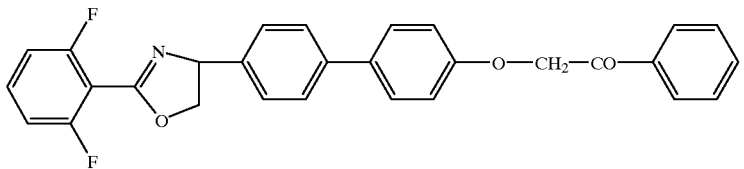

Formula (II) provides a general definition of the hydroxybiphenyloxazolines to be used as starting substances in the process according to the invention. In the formula (II), X, Y, Z, $R^1$, $R^2$, m and n preferably or particularly preferably have those meanings which have already been mentioned above as preferred or particularly preferred for these substituents and indices in connection with the description of the compounds of the formula (I) according to the invention.

The hydroxybiphenyloxazolines of the formula (II) are not yet known. However, some are the subject matter of earlier applications filed by the Applicant which do not yet belong to the prior art (cf., for example, German Patent Application with the file reference 44 44 108.1 of Dec. 12, 1994, which is related to U.S. Ser. No. 09/191,850, filed Nov. 19, 1998, U.S. Pat. No. 5,969,147), and/or can be obtained by generally known processes (cf., for example, EP-A-0 432 661, which is related to U.S. Pat. No. 5,141, 948), by a procedure in which amide derivatives of the formula (IV)

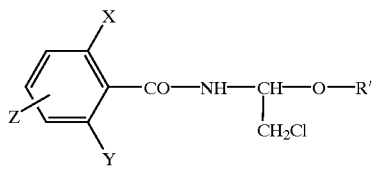

(IV)

in which

X, Y and Z have the abovementioned meaning and

R' represents $C_1$–$C_4$-alkyl, preferably methyl or ethyl, are reacted with biphenyl derivatives of the formula (V)

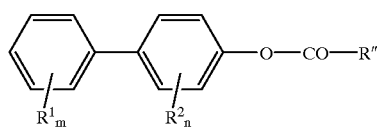

(V)

in which $R^1$, $R^2$, m and n have the abovementioned meanings and

R" represents $C_1$–$C_4$-alkyl or $C_1$–$C_4$-alkoxy, preferably methyl, ethyl, methoxy or ethoxy, in the presence of an acid catalyst such as, for example, sulfuric acid, acetic acid or aluminum chloride, and in the presence of a diluent, such as, for example, methylene chloride or acetonitrile, at temperatures between 0° C. and 80° C.;

the compounds thus obtained, of the formula (VI)

(VI)

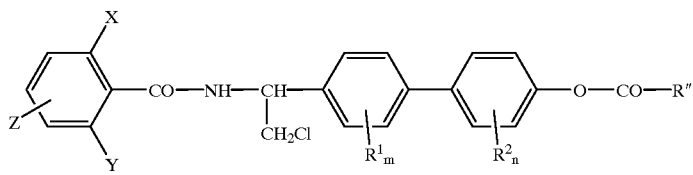

in which $R^1$, $R^2$, m, n, R", X, Y and Z have the abovementioned meaning, are cyclized in the presence of a base, such as, for example, sodium hydroxide solution, if appropriate in the presence of a catalyst, such as, for example, ammonia compounds, and if appropriate in the presence of a diluent, such as, for example, dimethylformamide, at temperatures between 0° C. and 100° C. to give biphenyloxazolines of the formula (VII)

(VII)

in which $R^1$, $R^2$, m, n, R", X, Y and Z have the abovementioned meaning, and these are hydrolyzed in the customary manner in the presence of a diluent, such as, for example, methanol, at room temperature, such as, for example, by means of aqueous ammonia solution, it also being possible for the cyclization and hydrolysis to be carried out in a one-pot reaction, if appropriate.

The amide derivatives of the formula (IV) are known (cf., for example, EP-A-0 594 179, which is related to U.S. Pat. No. 5,354,905) and/or can be obtained by the methods mentioned therein.

Formula (III) provides a general definition of the compounds also to be used as starting substances in the process according to the invention. In the formula (III), A preferably or particularly preferably has those meanings which have already been mentioned as preferred or particularly preferred for this substituent in connection with the description of the compounds of the formula (I) according to the invention.

M represents a customary leaving group, preferably halogen, in particular chlorine or bromine; alkylsulfonyloxy, in particular methylsulfonyloxy; or optionally substituted arylsulfonyloxy, in particular phenylsulfonyloxy, p-chlorophenylsulfonyloxy or tolylsulfonyloxy.

The compounds of the formula (III) are generally known compounds of organic chemistry.

Possible diluents for carrying out the process according to the invention are all the customary solvents. Solvents which can preferably be used are optionally halogenated, aromatic or aliphatic hydrocarbons, ketones, nitriles and amides. Examples which may be mentioned are toluene, acetone, acetonitrile, dimethylformamide and dimethylacetamide.

All the customary inorganic and organic bases are possible as the base for carrying out the process according to the invention. Examples which may be mentioned are tertiary amines, such as triethylamine, DBN (diazabicyclononene), DBU (diazabicycloundecene), DABCO (diazabicyclooctane), alkali metal and alkaline earth metal hydroxides, such as, for example, sodium hydroxide, potassium hydroxide and calcium hydroxide, and alkali metal and alkaline earth metal carbonates, such as, for example, sodium carbonate or potassium carbonate.

If appropriate, the process according to the invention is carried out in the presence of a phase transfer catalyst. Examples which may be mentioned are quaternary ammonium salts, such as tetraoctylammonium bromide or benzyltriethylammonium chloride, as well as tris(3,6-dioxaheptyl) amine (TDA).

The reaction temperatures can be varied within a substantial range in carrying out the process according to the invention. The reaction is in general carried out at temperatures between −20° C. and 100° C., preferably between 0° C. and 60° C.

In general, approximate equimolar amounts are used in carrying out the process according to the invention. However, it is also possible to use an excess of the compound of the formula (III).

Working up and isolation are carried out in the generally customary manner.

In some cases, it proves advantageous to obtain compounds of the formula (I) in which R represents one of the groupings (e) to (k) by generally customary and known derivatizations of the corresponding keto derivatives, carboxylic acid derivatives and nitriles, i.e. compounds of the formula (I) in which R represents cyano or one of the groupings (a) to (d).

The derivatizations which lead to ketals, thioketals, oximes, oxime ethers or hydrazones are particularly preferred here.

The compounds of the formula (I) according to the invention can also be obtained by a process in which A) in a first stage, compounds of the formula (VIII)

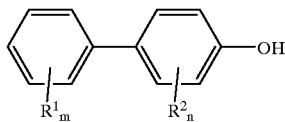

(VIII)

in which

R$^1$, R$^2$, m and n have the abovementioned meaning, are reacted with a compound of the formula (III)

M—A     (III)

in which

M and A have the abovementioned meaning, under the conditions of the process according to the invention;

B) in a second stage, the compounds thus obtained, of the formula (IX)

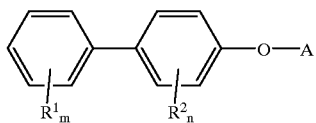

(IX)

in which

A, R$^1$, R$^2$, m and n have the abovementioned meaning, are reacted with acetyl chloride in the presence of a diluent, such as, for example, methylene chloride or dichloroethane, and in the presence of an acid or Lewis acid suitable for Friedel-Crafts reactions, such as, for example, tetrafluoroboric acid or aluminum chloride, at temperatures between −20° C. and +50° C.;

C) in a third stage, the compounds thus obtained, of the formula (X)

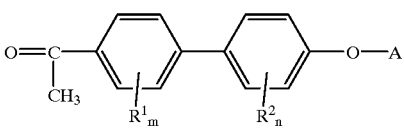

(X)

in which

A, R$^1$, R$^2$, m and n have the abovementioned meaning, are chlorinated or brominated, if appropriate in the presence of a diluent, such as, for example, methylene chloride or carbon tetrachloride, at temperatures between −10° C. and 25° C.;

D) in a fourth stage, the compounds thus obtained, of the formula (XI)

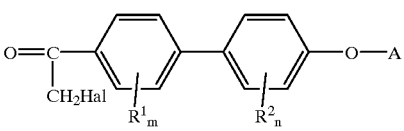

(XI)

in which

A, $R^1$, $R^2$, m and n have the abovementioned meaning and
Hal represents chlorine or bromine, are reacted with a salt of formic acid, such as, for example, sodium formate, in the presence of a diluent, if appropriate as a mixture with water, such as, for example, ethanol/water, and if appropriate in the presence of a phase transfer catalyst, such as, for example, quaternary ammonium salts, at temperatures between 50° C. and 150° C.;

E) in a fifth stage, the compounds thus obtained, of the formula (XII)

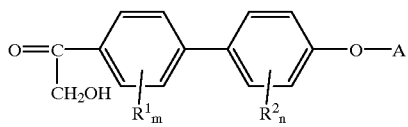

(XII)

in which

A, $R^1$, $R^2$, m and n have the abovementioned meaning, are reacted with O-methylhydroxylamine, if appropriate in the form of a salt, for example the hydrochloride, in the presence of a diluent, for example alcohols or ethers, and if appropriate in the presence of a base, for example sodium acetate, at temperatures between 0° C. and 60° C.;

F) in a sixth stage, the compounds thus obtained, of the formula (XIII)

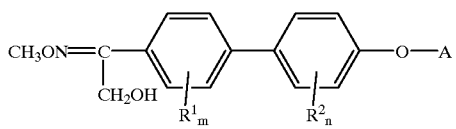

(XIII)

in which

A, $R^1$, $R^2$, m and n have the abovementioned meaning, are reacted with a reducing agent, such as, for example, sodium boronate, in the presence of an acid, such as, for example, trifluoroacetic acid, and if appropriate in the presence of a diluent, such as, for example, tetrahydrofuran, at temperatures between 0° C. and 120° C.;

G) in a seventh stage, the compounds thus obtained, of the formula (XIV)

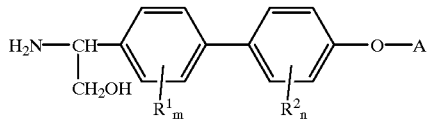

(XIV)

in which

A, $R^1$, $R^2$, m and n have the abovementioned meaning, are reacted with benzoyl chlorides of the formula (XV)

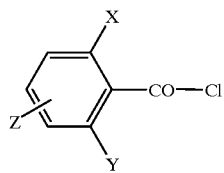

(XV)

in which

X, Y and Z have the abovementioned meaning, if appropriate in the presence of a base, such as, for example, triethylamine, and if appropriate in the presence of a diluent, such as, for example, tetrahydrofuran, at temperatures between 0° C. and 100° C.;

H) in an eighth stage, the compounds thus obtained, of the formula (XVI)

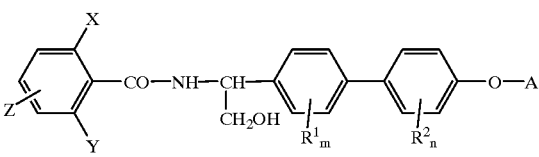

(XVI)

in which

A, $R^1$, $R^2$, m, n, X, Y and Z have the abovementioned meaning, are reacted with a chlorinating agent, such as, for example, thionyl chloride, if appropriate in the presence of a diluent, such as, for example, toluene, at temperatures between 20° C. and 100° C.;

I) in a ninth stage, the compounds thus obtained, of the formula (XVII)

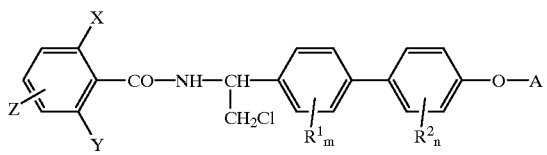

(XVII)

in which

A, $R^1$, R , m, n, X, Y and Z have the abovementioned meaning, are cyclized in the presence of a base, such as, for example, sodium hydroxide solution, if appropriate in the presence of a phase transfer catalyst, such as, for example, ammonium compounds, and if appropriate in the presence of a diluent, such as, for example, dimethylformamide, at temperatures between 0° C. and 100° C., to give the compounds of the formula (I) according to the invention.

The compounds of the formula (XVII) can also be obtained directly by reacting amide derivatives of the formula (IV) with compounds of the formula (IX) in the presence of an acid catalyst, such as, for example, hydrogen fluoride, boron trifluoride or aluminum chloride, and in the presence of a diluent, such as, for example, methylene chloride or acetonitrile, at temperatures between 0° C. and 80° C.

The starting substances of the formula (VEII) are known and/or can be prepared in a simple manner by known methods.

The compounds of the formula (VIII) are obtained, for example, by sulfonating optionally substituted biphenyls and then reacting the products with alkali metal hydroxides to give the hydroxybiphenyls, or diazotizing aminobiphenyls and boiling the products (cf., for example, Houben-Weyl, Volume VI/1c (1976), page 216 and 251).

The benzoyl chlorides of the formula (XV) are generally known compounds of organic chemistry.

The compounds of the formulae (X), (XI), (XII), (XIII), (XIV), (XVI) and (XVII) which occur as intermediate products are not yet known and the invention also relates to these.

The active compounds are suitable for controlling animal pests, in particular insects, arachnids and nematodes which are encountered in agriculture, in forestry, in the preservation of stored products and of materials, and in the hygiene sector, while being well tolerated by crops and of favorable toxicity to warm-blooded animals. They can preferably be wed as crop protection products. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The compounds of the formula (I) according to the invention are distinguished in particular by a high insecticidal and acaricidal activity.

They can be used with particularly good success for controlling phytopathogenic insects, such as, for example, against the mustard beetle larvae (*Phaedon cochlaeriae*), caterpillars of the diamond-back moth (*Plutella maculipennis*), the peach aphid (*Myzus persicae*) and caterpillars of the owlet moth (*Spodoptera frugiperda*), or for controlling phytopathogenic mites, such as, for example, against the common spider mite (*Tetranychus urticae*).

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and very fine capsules in polymeric substances.

These formulations are produced in a known manner, for example by mixing the active compounds with extenders, that is, liquid solvents and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water, As solid carriers there are suitable:

For example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Particularly favorable mixing partners are, for example, the following:

Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-di-chloro-N-(4-trifluoromethylbenzyl)-benzamide; (E)-2-methoxyimino-N-methyl-2-(2-phenoxyphenyl)-acetamide; 8-hydroxyquinoline sulfate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazime, carboxin, chinomethionat (quinomethionate), chloroneb, chloropicrin, chlorothalonil, chlozolinate, cufraneb, cymoxanil, cyproconazole, cyprofuram, dichlorophen, diclobutrazole, diclofluanid, diclomezin, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazole, imazalil, imibenconazole, iminoctadine, iprobenfos (IBP), iprodione, isoprothiolane, kasugamycin, copper formulations, such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur formulations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:
bronopol, dichlorophen, nitrapyrin, nickel dimethyldithiocarbamate, kasugamycin, octhilinone, furanecarboxylic acid, oxytetracycline, probenazole, streptomycin, tecloftalam, copper sulfate and other copper formulations.

Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators is also possible.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention act not only against plant and hygiene pests and pests of stored products, but also in the veterinary medicine sector against animal parasites (ectoparasites), such as hard ticks, soft ticks, mange mites, harvest mites, flies (biting and licking), parasitic fly larvae, lice, biting lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they show a good development-inhibiting action against fly larvae of *Lucilla cuprina*.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and so-called experimental animals, such as, for example, hamsters, guinea pigs, rats and mice. By controlling these arthropods, cases of death and reductions in productivity (for meat, milk, wool, hides, eggs, honey and the like) should be diminished, so that more economical and easier animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear tags, tail tags, limb bands, halters, marking devices and the like.

When used for livestock, poultry, pets and the like, the active compounds of the formula (I) can be used as formulations (for example powders, emulsions, free-flowing compositions) which comprise the active compounds in an amount of 1 to 80% by weight, directly or after 100- to 10,000-fold dilution, or they can be used as a chemical bath.

The preparation and the use of the active compounds according to the invention can be seen from the following examples.

PREPARATION EXAMPLES

Example 1

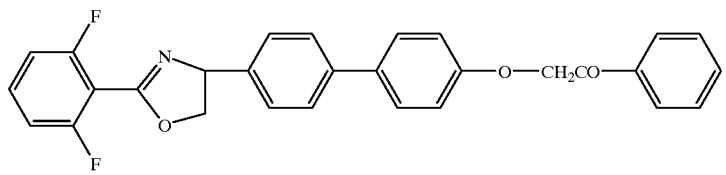

3.51 g (0.01 mol) of 2-(2,6-difluorophenyl)-4-(4'-hydroxy-biphenyl-4-yl)-1,3-oxazoline, 2.0 g (0.01 mol) of benzoylmethyl bromide and 1.38 g (0.01 mol) of potassium carbonate are suspended in 50 ml of acetonitrile. After addition of three drops of tris(3,6-dioxaheptyl)amine (TDA), the reaction mixture is stirred at 80° C. for 18 hours and then concentrated. The residue is taken up in 100 ml of methylene chloride, the mixture is washed with water, dried over sodium sulfate and concentrated and the residue is purified by column chromatography with methylene chloride as the mobile phase.

1.7 g (36.2% of theory) of 2-(2,6-difluorophenyl)-4-(4'-benzoylmethoxy-biphenyl-4-yl)-1,3-oxazoline of melting point m.p.: 78–82° C. are obtained.

Preparation of the Starting Substance

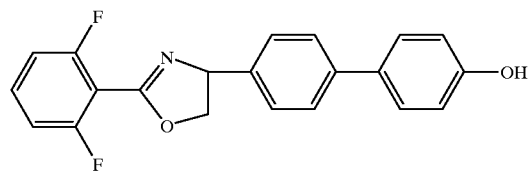

10.9 g (0.026 mol) of 2-(2,6-difluorophenyl)-4-(4'-ethoxycarbonyloxybiphenyl-4-yl)-1,3-oxazoline are suspended in 50 ml of methanol, and 35.4 ml (0.52 mol) of 25% strength aqueous ammonia solution are then added dropwise at room temperature. After 28 hours at room temperature, the precipitate is filtered off with suction and washed with a little methanol.

Yield 7.6 g (97.4% of theory), m.p.: 180 to 182° C.

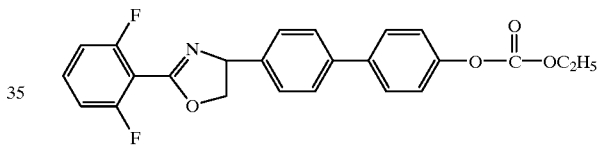

4 ml (0.045 mol) of 50% strength sodium hydroxide solution are added dropwise to 19.8 g (0.043 mol) of 2-(2,6-difluorobenzoylamido)-2-(4'-ethoxycarbonyloxybiphenyl-4-yl)-1-chloroethane in 120 ml of dimethyl formamide. After 2 hours at room temperature, the mixture is stirred into 500 ml of ice-water and the crystals which have precipitated out are filtered off with suction.

Yield: 15.1 g (83% of theory), m.p.: 98 to 100° C.

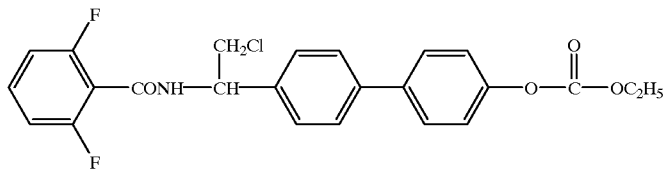

130.4 g (0.98 mol) of aluminum chloride are introduced in portions into a mixture of 53 g (0.213 mol) of 2-(2,6-difluorobenzoylamido)-2-methoxy-1-chloroethane, 48.4 g (0.2 mol) of 4-ethoxycarbonyloxybiphenyl and 12 ml of glacial acetic acid in 200 ml of methylene chloride at 5° C. in the course of 30 minutes. During this operation, the batch changes color via blue to red-violet. The reaction mixture is stirred at 5° C. for one hour and at 10° C. for 1 hour and poured cautiously onto ice, the suspension is decanted cautiously from the water and concentrated on a rotary evaporator, 50 ml of acetonitrile are added to the residue and the crystals which have precipitated out are filtered off with suction.

Yield 42.8 g (47% of theory), m.p.: 209° C.

Example 2

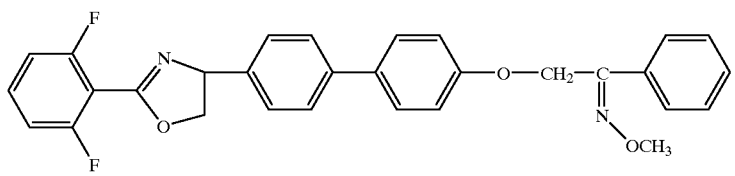

0.167 g (0.002 mol) of O-methylhydroxylamine hydrochloride and 0.164 g (0.002 mol) of sodium acetate are added to 0.96 g (0.002 mol) of 2-(2,6-difluorophenyl)-4-(4'-benzoylmethoxy-biphenyl-4-yl)-1,3-oxazoline (Example 1) in 20 ml of methanol. The reaction mixture is stirred at 65° C. for 6 hours and then concentrated. The residue is taken up in 20 ml of methylene chloride and the mixture is washed with water, dried over sodium sulfate and concentrated. The oily residue is purified by column chromatography (mobile phase: toluene/ether: 8/2).

0.7 g (70% of theory) of 2-(2,6-difluorophenyl)-4-[4'-(2-methoximino-2-phenyl)-ethoxy-biphenyl-4]-4-yl)-1,3-oxazoline with a log p=5.01 is obtained.

[log p=logarithm of the partition coefficient p of the substance between the solvents octanol and water, determined experimentally from reversed phase HPLC]

Example 3

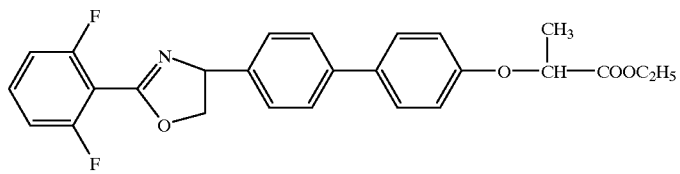

3.51 g (0.01 mol) of 2-(2,6-difluorophenyl)-4-(4'-hydroxybiphenyl-4-yl)-1,3-oxazoline and 1.38 g (0.01 mol) of potassium carbonate are suspended in 50 ml of acetonitrile and, after addition of three drops of tris(3,6-dioxaheptyl)amine (TDA), 1.8 g (0.01 mol) of ethyl 2-bromopropionate are added. The reaction mixture is stirred at 65° C. for 18 hours and then concentrated. The residue is taken up in 100 ml of methylene chloride, and the mixture is washed with water, dried over sodium sulfate and concentrated. The oily residue is purified by column chromatography with methylene chloride as the mobile phase.

2.5 g (55.4% of theory) of 2-(2,6-difluorophenyl)-4-[4'-(1-ethoxycarbonyl-eth-1-yl-oxy)-biphenyl-4-yl]-1,3-oxazoline with a log p=4.12 are obtained.

Example 4

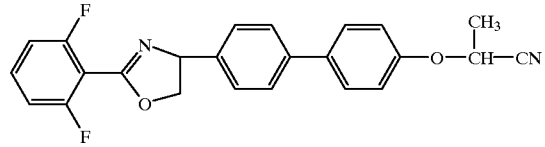

3.51 g (0.01 mol) of 2-(2,6-difluorophenyl)-4-(4'-hydroxybiphenyl-4-yl)-1,3-oxazoline and 1.38 g (0.01 mol) of potassium carbonate are suspended in 50 ml of acetonitrile and, after addition of three drops of tris(3,6-dioxaheptyl)amine (TDA), 0.9 g (0.01 mol) of 2-chloropropionitrile is added. The reaction mixture is stirred at 80° C. for 20 hours and then concentrated. The residue is taken up in 100 ml of methylene chloride and the mixture is washed with water, dried over sodium sulfate and concentrated. The oily residue is purified by column chromatography with methylene chloride as the mobile phase.

2.6 g (64.4% of theory) of 2-(2,6-difluorophenyl)-4-[4'-(2-propionitriloxy)-biphenyl-4-yl]-1,3-oxazoline of melting point 100–120° C. are obtained.

Example 5

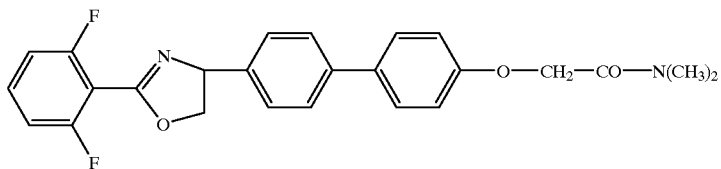

3.51 g (0.01 mol) of 2-(2,6-difluorophenyl)-4-(4'-hydroxybiphenyl-4-yl)-1,3-oxazoline and 1.38 g (0.01 mol) of potassium carbonate are suspended in 50 ml of acetonitrile and, after addition of three drops of tris(3,6-dioxaheptyl)amine (TDA), 1.2 g (0.01 mol) of 2-chloro-N,N-dimethyl-acetamide are added. The reaction mixture is stirred at 80° C. for 20 hours and then concentrated. The residue is taken up in 100 ml of methylene chloride and the mixture is washed with water, dried over sodium sulfate and concentrated. The residue is stirred with diisopropyl ether and the mixture is concentrated.

2.4 g (55% of theory) of 2-(2,6-difluorophenyl)-4-(4'-dimethylaminocarbonylmethyloxy-biphenyl-4-yl)-1,3-oxazoline of melting point 78–80° C. are obtained.

The compounds of the formula (I) shown in the following table are obtained analogously to Examples 1 to 5 and in accordance with the general preparation instructions:

TABLE 1

(I)

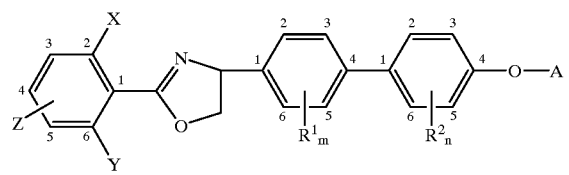

| Ex. No. | X | Y | Z | $R^1_m$ | $R^2_n$ | A | m.p. (° C.[1]) or log p |
|---|---|---|---|---|---|---|---|
| 6  | F | F | H | H | H | —$CH_2$—$COOCH_3$ | 125–28[1] |
| 7  | F | F | H | H | H | —$CH_2$—$COCH_3$  | 120–25[1] |
| 8  | F | F | H | H | H |                   | 120–22[1] |
| 9  | F | F | H | H | H | —$CH_2$—$COOC_2H_5$ | 115–18[1] |
| 10 | F | F | H | H | H | —$CH_2$—$COOC_4H_9$-t | 4.43 |
| 11 | F | F | H | H | H | —CH($C_2H_5$)—$COOC_2H_5$ | 4.53 |
| 12 | F | F | H | H | H | —CH($CH_3$)—$COOC_2H_5$ | 3.80 |
| 13 | F | F | H | H | H | —$CH_2$—C($CH_3$)=$NOCH_3$ | 70[1] |
| 14 | F | F | H | H | H | —$CH_2$—$CH_2$—$CH_2$—CN | 95–98[1] |
| 15 | F | F | H | H | H | —$CH_2$—CO—N($C_2H_5$)$_2$ | 3.35 |
| 16 | F | F | H | H | H | —$CH_2$—$CH_2$—CH(O$C_2H_5$)$_2$ | 4.74 |
| 17 | F | F | H | H | H | —CH($C_3H_7$-i)—CN | 4.45 |
| 18 | F | F | H | H | H | —CH($C_3H_7$-i)—$COOCH_3$ | 4.56 |
| 19 | F | F | H | H | H | —CH($C_2H_5$)—$COOCH_3$ | 4.18 |

TABLE 1-continued

| Ex. No. | X | Y | Z | $R^1_m$ | $R^2_n$ | A | m.p. (° C.)[1]) or log p |
|---|---|---|---|---|---|---|---|
| 20 | F | F | H | H | H | —CH(CH$_3$)— attached to 2-position of 5,6-dihydro-1,4,2-dioxazine ring | 70[1]) |
| 21 | F | F | H | H | H | —CH(C$_3$H$_7$)—CN | 110–14[1]) |
| 22 | F | F | H | H | H | —CH$_2$—CO—cyclopropyl | 120–22[1]) |
| 23 | F | F | H | H | H | —CH(CH$_3$)—C(CH$_3$)=NOCH$_3$ | 4.62 (A isomer)* <br> 4.71 (B isomer)* |
| 24 | F | F | H | H | H | —CH$_2$—C(cyclopropyl)=NOCH$_3$ | 4.90 (E isomer) |
| 25 | F | F | H | H | H | —CH$_2$—C(CH$_3$)=NOC$_2$H$_5$ | 47.0 (A isomer)* <br> 4.76 (B isomer)* |
| 26 | F | F | H | H | H | —CH$_2$—C(cyclopropyl)=NOCH$_3$ | 4.90 (A isomer)* <br> 4.56 (B isomer)* |
| 27 | F | F | H | H | H | —CH$_2$—C(phenyl)=NOCH$_3$ | 4.74 (A isomer)* |
| 28 | F | F | H | H | H | —CH$_2$—CO—N(CH$_3$)(4-Cl-C$_6$H$_4$) | 60–65[1]) |
| 29 | F | F | H | H | H | —CH$_2$—CO—N(CH$_3$)(C$_6$H$_5$) | 155–60[1]) |
| 30 | F | F | H | H | H | —CH$_2$—CO—NH(C$_3$H$_7$-i) | 156[1]) |
| 31 | F | F | H | H | H | —CH$_2$—CO—N(CH$_3$)(3-Cl-C$_6$H$_4$) | 110–14[1]) |
| 32 | F | F | H | H | H | —CH$_2$—CO—N(CH$_3$)(3-CF$_3$-C$_6$H$_4$) | $n_D^{20}$ = 1.5644 |

TABLE 1-continued
| | | | | | | | |
|---|---|---|---|---|---|---|---|
| 33 | F | F | H | H | H | 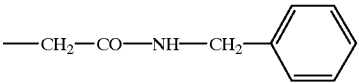 —CH₂—CO—NH—CH₂—C₆H₅ | 142–44[1)] |
| 34 | F | F | H | H | H | 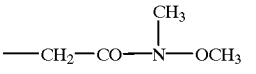 —CH₂—CO—N(CH₃)(OCH₃) | 3.07<br>185–88[1)] |
| 35 | F | F | H | H | H | —CH₂—CO—NH₂ | 185–88[1)] |
| 36 | F | F | H | H | H | 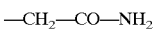 —CH₂—CO—NH—(2,6-di-C₂H₅-C₆H₃) | 110–12[1)] |
| 37 | F | F | H | H | H | 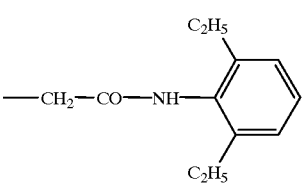 —CH₂—CO—NH—(4-F-C₆H₄) | 150–55[1)] |
| 38 | F | F | H | H | H | —CH₂—CO—NH—C₄H₉-t | 110[1)] |
| 39 | F | F | H | H | H | 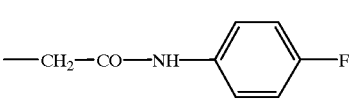 —CH₂—CO—NH—C₆H₅ | 155–58[1)] |
| 40 | F | F | H | H | H | 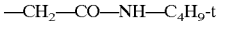 —CH₂—CO—NH—(4-Cl-C₆H₄) | 164–66[1)] |
| 41 | F | F | H | H | H | 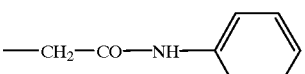 —CH₂—CO—NH—(3,5-di-Cl-C₆H₃) | 157–60[1)] |
| 42 | F | F | H | H | H | 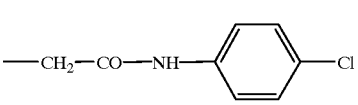 —CH₂—CO—NH—(4-OC₂H₅-C₆H₄) | 168–70[1)] |
| 43 | F | F | H | H | H | —CH₂—CH(OC₂H₅)₂ | 4.44 |
| 44 | F | F | H | H | H | 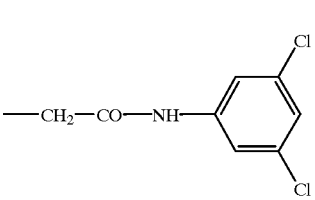 —CH₂—CO—NH—(2,4-di-Cl-C₆H₃) | 202[1)] |
| 45 | F | F | H | H | H | 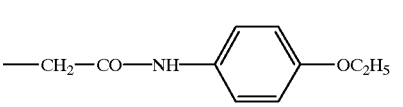 —CH₂—CO—NH—(3,4-di-CN-C₆H₃) | 232–34[1)] |
| 46 | F | F | H | H | H |  —CH₂—CO—NH—C(CH₃)(CF₃) | 148–50[1)] |
| 47 | F | F | H | H | H | —CH₂—CO—N(CH₂CH=CH₂)₂ | 3.76 |

TABLE 1-continued
| 48 | F | F | H | H | H | 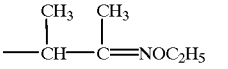 | 5.02 (A isomer)*<br>5.13 (B isomer)* |
|---|---|---|---|---|---|---|---|
| 49 | H | Cl | H | H | H | 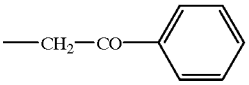 | 4.38 |
| 50 | H | Cl | H | H | H | —CH$_2$CO—CH$_3$ | 70–72[1)] |
| 51 | H | Cl | H | H | H | 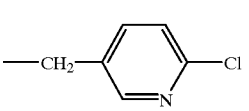 | 135–37[1)] |
| 52 | H | Cl | H | H | H | 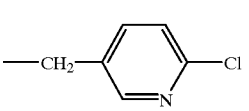 | 5.40 |
| 53 | H | Cl | H | H | H | 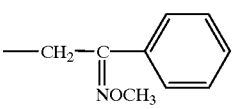 | 80–85[1)] |
| 54 | F | F | H | H | H | 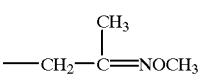 | 4.04 |
| 55 | F | F | H | H | H | 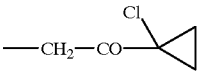 | 5.09 (A isomer)*<br>4.78 (B isomer)* |
| 56 | F | F | H | H | H | 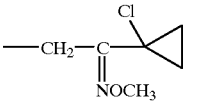 | 5.28 (A isomer)*<br>4.92 (B isomer)* |
| 57 | F | F | H | H | H | 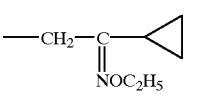 | 5.49 (A isomer)*<br>4.85 (B isomer)* |
| 58 | Cl | H | H | H | H | 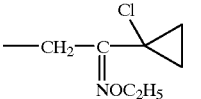 | 77–79[1)] |
| 59 | Cl | H | H | H | H | 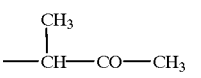 | 5.44 (A isomer)*<br>5.56 (B isomer)* |
| 60 | F | F | H | H | H | 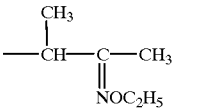 | 95–96[1)] |
| 61 | F | F | H | H | H | 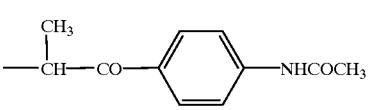 | 5.24 |
| 62 | Cl | F | H | H | H | 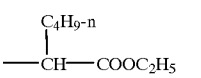 | 5.31 (A isomer)*<br>5.42 (B isomer)* |

TABLE 1-continued

| | | | | | | | |
|---|---|---|---|---|---|---|---|
| 63 | Cl | F | H | H | H | —CH(CH₃)—CO—CH₃ | 112–15[1] |
| 64 | F | F | H | H | H | —CH(CH₃)—C(CH₃)=N—OH | 3.48 (A isomer)*<br>3.54 (B isomer)* |
| 65 | F | F | H | H | H | —CH₂—COC₂H₅ | 122–24[1] |
| 66 | F | F | H | H | H | —CH₂—C(C₂H₅)=NOC₂H₅ | 4.98 (A isomer)*<br>4.90 (B isomer)* |
| 67 | F | F | H | H | H | —CH₂—C(cyclopropyl)=NOC₂H₅ | 4.72 (A isomer)*<br>4.61 (B isomer)* |
| 68 | F | F | H | H | H | —CH₂—CO—C(CH₃)₂C₃H₇-i | 4.55 |
| 69 | F | F | H | H | H | —CH(CH₃)—C(CH₃)=NOC₃H₇-i | 4.47 |
| 70 | F | F | H | H | H | —CH(CH₃)—C(CH₃)=NOC₂H₅ | 5.12 |
| 71 | F | F | H | H | H | —CH₂—CO—C(CH₃)₂CHCl₂ | 4.55 |
| 72 | F | F | H | H | H | —CH₂—CO—C₄H₉-t | 101–02[1] |
| 73 | F | F | H | H | H | —CH₂—CO—C₃H₇-i | 86–88[1] |
| 74 | F | F | H | H | H | —C(CH₃)₂—COCH₃ | 102–06[1] |
| 75 | F | F | H | H | H | —CH₂—CO—C(CH₃)₂—CH=CCl₂ | 92–94[1] |
| 76 | F | F | H | H | H | —CH₂—C(CH₃)=NOH | 129–36[1] |
| 77 | Cl | F | H | H | H | —CH₂—COCH₃ | 92[1] |
| 78 | F | F | H | H | H | —CH₂—C(C₃H₇-i)=NOC₂H₅ | 5.72 (A isomer)*<br>5.49 (B isomer)* |
| 79 | F | F | H | H | H | —CH₂—C(C₄H₉-t)=NOC₂H₅ | 5.95 |
| 80 | F | F | H | H | H | —CH₂—C(CH₃)=NOC₃H₇-i | 5.10 (A isomer)*<br>5.17 (B isomer)* |
| 81 | Cl | F | H | H | H | —CH₂—C(CH₃)=NOC₂H₅ | 4.98 |
| 82 | F | F | H | H | H | —CH₂—C(CH₃)=NOCH₂C₆H₅ | 5.15 (A isomer)*<br>(B isomer)* |
| 83 | F | F | H | H | H | —CH₂—C(CH₃)=NOC₂H₅ | 5.49 (A isomer)*<br>5.56 (B isomer)* |
| 84 | F | F | H | H | 3-Cl | —CH₂—COCH₃ | 118–19[1] |

TABLE 1-continued

| # | | | | | | Group | Value |
|---|---|---|---|---|---|---|---|
| 85 | Cl | H | H | H | H | —CH(CH$_3$)—C(CH$_3$)=NOC$_2$H$_5$ | 5.40 |
| 86 | F | F | H | H | 3-Cl | —CH$_2$—C(CH$_3$)=NOCH$_3$ | 4.79 (A isomer)*  4.70 (B isomer)* |
| 87 | F | F | H | H | 3-Cl | —CH$_2$—C(CH$_3$)=NOC$_2$H$_5$ | 5.39 (A isomer)*  5.19 (B isomer)* |
| 88 | F | F | H | H | H | —CH(CH$_3$)—C(CH$_3$)=NOCH$_2$—CH=CH$_2$ | 5.04 (A isomer)*  5.13 (B isomer)* |
| 89 | F | F | H | H | H | —CH$_2$—C(CH$_3$)=NOCH$_2$—CH=CH$_2$ | 4.78 (A isomer)*  4.72 (B isomer)* |
| 90 | F | F | H | H | 3-Cl | —CH$_2$—C(Ph)=NOCH$_3$ | 95[1)] |
| 91 | F | F | H | H | 3-Cl | —CH(CN)C$_3$H$_7$-n | 4.87 |
| 92 | F | F | H | H | 3-Cl | —(CH$_2$)$_3$—CN | 108–11[1)] |
| 93 | F | Cl | H | H | H | —CH$_2$—CO—Ph | 4.28 |
| 94 | F | Cl | H | H | H | —CH$_2$—C(Ph)=NOCH$_3$ | 5.25 |
| 95 | F | F | H | H | 3-Cl | —CH(CH$_3$)—CN | 4.06 |
| 96 | F | F | H | H | 3-Cl | —CH$_2$—(6-Cl-pyridin-3-yl) | 107–109[1)] |
| 97 | F | F | H | H | 3-Cl | —CH$_2$CH$_2$CH(OC$_2$H$_5$)$_2$ | 5.12 |
| 98 | F | F | H | H | H | —CH$_2$—(2-methyl-1,3-dioxolan-2-yl) | 3.77 |
| 99 | F | F | H | H | H | —C(CH$_3$)$_2$—C(CH$_3$)=NOC$_2$H$_5$ | 5.57 |
| 100 | F | F | H | H | H | —C(CH$_3$)$_2$—C(CH$_3$)=NOCH$_3$ | 5.14 |
| 101 | F | F | H | H | 3-Cl | —CH(CH$_3$)—COCH$_3$ | 4.15 |

TABLE 1-continued
| 102 | F | F | H | H | 3-Cl | 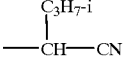 —CH(C₃H₇-i)—CN | 4.84 |
| 103 | F | F | H | H | H | 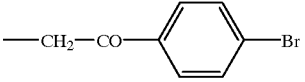 —CH₂—CO—C₆H₄—Br (4-) | 121–23[1)] |
| 104 | F | F | H | H | H | 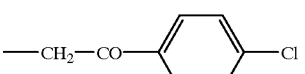 —CH₂—CO—C₆H₄—Cl (4-) | 154–55[1)] |
| 105 | F | F | H | H | H | 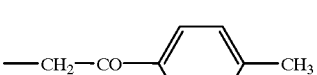 —CH₂—CO—C₆H₄—CH₃ (4-) | 124–25[1)] |
| 106 | F | F | H | H | H | 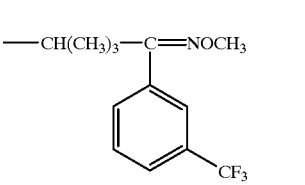 —CH(CH₃)₃—C(=NOCH₃)—C₆H₄—CF₃ (3-) | 5.50 |
| 107 | F | F | H | H | H | 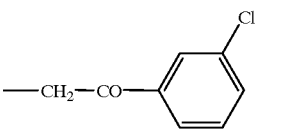 —CH₂—CO—C₆H₄—Cl (3-) | 82–84[1)] |
| 108 | F | F | H | H | H | 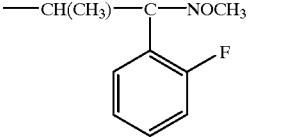 —CH(CH₃)—C(=NOCH₃)—C₆H₄—F (2-) | 5.01 |
| 109 | F | F | H | H | H | 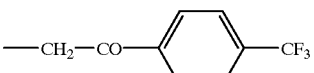 —CH₂—CO—C₆H₄—CF₃ (4-) | 142–44[1)] |
| 110 | F | F | H | H | H | 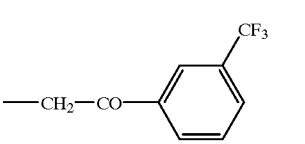 —CH₂—CO—C₆H₄—CF₃ (3-) | 116–18[1)] |
| 111 | F | F | H | H | H | 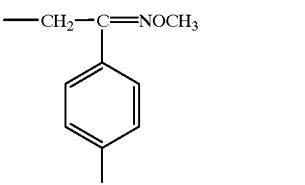 —CH₂—C(=NOCH₃)—C₆H₄—CF₃ (4-) | 5.53 |
| 112 | F | F | H | H | H | 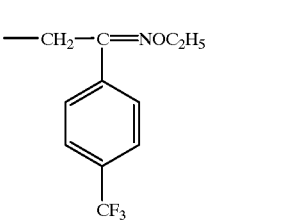 —CH₂—C(=NOC₂H₅)—C₆H₄—CF₃ (4-) | 5.87 (A-Isomer)* 5.57 (B-Isomer)* |

TABLE 1-continued

| No. | | | | | | R | Value |
|---|---|---|---|---|---|---|---|
| 113 | H | Cl | H | H | 3-Cl | —CH(CH$_3$)—COCH$_3$ | 4.51 |
| 114 | F | F | H | H | H | —CH$_2$—CO—C$_6$H$_3$(OCHF$_2$)- (4-OCHF$_2$-phenyl) | 4.16 |
| 115 | F | F | H | H | H | —CH$_2$—C(=NOCH$_3$)—(3-Cl-phenyl) | 5.52 (A-Isomer)* <br> 5.19 (B-Isomer)* |
| 116 | F | F | H | H | H | —CH$_2$—C(=NOC$_2$H$_5$)—(3-Cl-phenyl) | 5.89 (A-Isomer)* <br> 5.54 (B-Isomer)* |
| 117 | F | F | H | H | H | —CH$_2$—CO—(3-CH$_3$-4-Cl-phenyl) | 4.86 |
| 118 | F | F | H | H | H | —CH$_2$—C(=NOC$_2$H$_5$)—(4-Br-phenyl) | 5.65 (A-Isomer)* <br> 5.57 (B-Isomer)* |
| 119 | F | F | H | H | H | —CH$_2$—C(=NOC$_2$H$_5$)—(4-Br-phenyl) | 6.03 (A-Isomer)* <br> 5.72 (B-Isomer)* |
| 120 | F | Cl | H | H | H | —CH(CH$_3$)—C(CH$_3$)=NOCH$_2$CH=CH$_2$ | 5.70 (A-Isomer)* <br> 5.81 (B-Isomer)* |
| 121 | F | F | H | H | H | —CH$_2$—C(=NOCH$_3$)—(3-CF$_3$-phenyl) | 5.80 (A-Isomer)* <br> 4.49 (B-Isomer)* |
| 122 | F | F | H | H | H | —CH$_2$—C(=NOC$_2$H$_5$)—(3-CF$_3$-phenyl) | 6.18 (A-Isomer)* <br> 5.87 (B-Isomer)* |
| 123 | F | Cl | H | H | H | —CH(CH$_3$)—C(CH$_3$)=NOC$_3$H$_7$-i | 6.15 (A-Isomer)* <br> 6.30 (B-Isomer)* |

TABLE 1-continued

| 124 | F | Cl | H | H | H | —CH$_2$—C(CH$_3$)=NOC$_3$H$_7$-i | 5.78 (A-Isomer)*<br>5.88 (B-Isomer)* |
| 125 | F | Cl | H | H | H | —CH$_2$—C(CH$_3$)=NOCH$_2$CH=CH$_2$ | 5.04 (A-Isomer)*<br>5.11 (B-Isomer)* |
| 126 | F | Cl | H | H | H | —CH$_2$—C(CH$_3$)=NOCH$_2$C$_6$H$_5$ | 5.45 (A-Isomer)*<br>5.53 (B-Isomer)* |
| 127 | F | F | H | H | 3-Cl | —CH(CH$_3$)—C(CH$_3$)=NOCH$_3$ | 5.06 (A-Isomer)*<br>5.15 (B-Isomer)* |
| 128 | F | F | H | H | H | —CH$_2$—CO—C$_6$H$_4$—OCH$_3$ | 135–37[1)] |
| 129 | F | F | H | H | H | —CH$_2$—CO—C$_6$H$_4$—CH$_2$C$_3$H$_7$-i | 118–20[1)] |
| 130 | F | F | H | H | H | —CH$_2$—C(=NOCH$_3$)(4-Cl-C$_6$H$_4$) | 5.27 (A-Isomer)*<br>5.54 (B-Isomer)* |
| 131 | F | F | H | H | H | —CH$_2$—C(=NOC$_2$H$_5$)(4-Cl-C$_6$H$_4$) | 5.61 (A-Isomer)*<br>5.54 (B-Isomer)* |
| 132 | F | F | H | H | H | —CH$_2$—CO—(2,5-Cl$_2$-C$_6$H$_3$) | 4.78 |
| 133 | F | F | H | H | H | —CH$_2$—C(=NOCH$_3$)(4-CH$_3$-C$_6$H$_4$) | 5.07 (A-Isomer)*<br>5.35 (B-Isomer)* |

TABLE 1-continued

| No. | | | | | | Structure | Values |
|---|---|---|---|---|---|---|---|
| 134 | F | F | H | H | H | —CH$_2$—C(=NOC$_2$H$_5$)—C$_6$H$_4$—CH$_3$(p) | 5.42 (A-Isomer)*<br>5.71 (B-Isomer)* |
| 135 | H | Cl | H | H | H | —CH$_2$—C(CH$_3$)=NOC$_3$H$_7$-i | 5.53 (A-Isomer)*<br>5.61 (B-Isomer)* |
| 136 | H | Cl | H | H | H | —CH(CH$_3$)—C(CH$_3$)=NOC$_3$H$_7$-i | 5.88 (A-Isomer)*<br>6.02 (B-Isomer)* |
| 137 | H | Cl | H | H | H | —CH$_2$—C(CH$_3$)=NOCH$_2$—C$_6$H$_5$ | 5.55 (A-Isomer)*<br>5.62 (B-Isomer)* |
| 138 | F | F | H | H | H | —CH$_2$—C(=NOCH$_3$)—C$_6$H$_4$—CHF$_2$(p) | 4.78 (A-Isomer)*<br>4.98 (B-Isomer)* |
| 139 | F | F | H | H | H | —CH$_2$—C(=NOC$_2$H$_5$)—C$_6$H$_4$—CHF$_2$(p) | 5.07 (A-Isomer)*<br>5.31 (B-Isomer)* |
| 140 | F | F | H | H | H | —CH$_2$—C(=NOCH$_3$)—C$_6$H$_3$(3-CH$_3$)(4-Cl) | 5.57 (A-Isomer)*<br>5.88 (B-Isomer)* |
| 141 | F | F | H | H | H | —CH$_2$—C(=NOC$_2$H$_5$)—C$_6$H$_3$(3-CH$_3$)(4-Cl) | 5.93 (A-Isomer)*<br>6.23 (B-Isomer)* |
| 142 | H | Cl | H | H | H | —CH$_2$—C(CH$_3$)=NOCH$_2$—CH=CH$_2$ | 5.12 (A-Isomer)*<br>5.20 (B-Isomer)* |
| 143 | H | Cl | H | H | H | —CH(CH$_3$)—C(CH$_3$)=NOCH$_2$—CH=CH$_2$ | 5.45 (A-Isomer)*<br>5.57 (B-Isomer)* |

TABLE 1-continued

| 144 | H | Cl | H | H | 3-Cl | —CH(CH$_3$)—C(CH$_3$)=NOC$_2$H$_5$ | 5.83 (A-Isomer)*<br>6.01 (B-Isomer)* |
| --- | --- | --- | --- | --- | --- | --- | --- |
| 145 | H | Cl | H | H | 3-Cl | —CH(CH$_3$)—C(CH$_3$)=NOC$_3$H$_7$-i | 6.30 (A-Isomer)*<br>6.44 (B-Isomer)* |
| 146 | F | F | H | H | 3-Cl | —CH(CH$_3$)—C(CH$_3$)=NOC$_3$H$_7$-i | 5.87 (A-Isomer)*<br>6.00 (B-Isomer)* |
| 147 | F | F | H | H | 3-Cl | —CH(CH$_3$)—C(CH$_3$)=NOCH$_2$—CH=CH$_2$ | 5.49 (A-Isomer)*<br>5.58 (B-Isomer)* |
| 148 | F | F | H | H | H | —CH$_2$—CO—(3,4-di-CH$_3$-C$_6$H$_3$) | 4.62 |
| 149 | F | F | H | H | H | —CH$_2$—C(=NOCH$_3$)—(4-OCH$_3$-C$_6$H$_4$) | 4.70 (A-Isomer)*<br>4.91 (B-Isomer)* |
| 150 | F | F | H | H | H | —CH$_2$—C(=NOC$_2$H$_5$)—(4-OCH$_3$-C$_6$H$_4$) | 5.04 (A-Isomer)*<br>5.27 (B-Isomer)* |
| 151 | F | Cl | H | H | H | —C(CH$_3$)$_2$—COCH$_3$ | 4.48 |
| 152 | H | Cl | H | H | H | —C(CH$_3$)$_2$—COCH$_3$ | 4.56 |
| 153 | F | F | H | H | 3-Cl | —C(CH$_3$)$_2$—COCH$_3$ | 4.61 |
| 154 | F | F | H | H | H | —CH$_2$—C(=NOCH$_3$)—(4-CH$_2$-C$_3$H$_7$-i-C$_6$H$_4$) | 6.34 (A-Isomer)*<br>6.05 (B-Isomer)* |
| 155 | F | F | H | H | H | —CH$_2$—C(=NOC$_2$H$_5$)—(4-CH$_2$-C$_3$H$_7$-i-C$_6$H$_4$) | 6.70 (A-Isomer)*<br>6.36 (B-Isomer)* |
| 156 | F | F | H | H | H | —CH$_2$—CO—(4-OCF$_2$—CHF$_2$-C$_6$H$_4$) | 84–85[1)] |

TABLE 1-continued

| 157 | F | F | H | H | H | —CH₂—C(=NOCH₃)—C₆H₄—OCF₂—CHF₂ | 5.28 (A-Isomer)* 5.04 (B-Isomer)* |
| --- | --- | --- | --- | --- | --- | --- | --- |
| 158 | F | F | H | H | H | —CH₂—C(=NOC₂H₅)—C₆H₄—OCF₂—CHF₂ | 5.59 (A-Isomer)* 5.35 (B-Isomer)* |
| 159 | F | Cl | H | H | H | —C(CH₃)₂—C(CH₃)=NOH | |
| 160 | F | Cl | H | H | H | —C(CH₃)₂—C(CH₃)=NOCH₃ | 5.45 |
| 161 | F | Cl | H | H | H | —C(CH₃)₂—C(CH₃)=NOC₂H₅ | 5.88 |
| 162 | F | Cl | H | H | H | —C(CH₃)₂—C(CH₃)=NOC₃H₇-i | |
| 163 | H | Cl | H | H | H | —C(CH₃)₂—C(CH₃)=NOH | |
| 164 | H | Cl | H | H | H | —C(CH₃)₂—C(CH₃)=NOCH₃ | |
| 165 | H | Cl | H | H | H | —C(CH₃)₂—C(CH₃)=NOC₂H₅ | |
| 166 | H | Cl | H | H | H | —C(CH₃)₂—C(CH₃)=NOC₃H₇-i | |
| 167 | F | F | H | H | H | —C(CH₃)₂—C(CH₃)=NOH | 3.82 (A-Isomer)* 3.39 (B-Isomer)* |
| 168 | F | F | H | H | H | —C(CH₃)₂—C(CH₃)=NOC₃H₇-n | |
| 169 | F | F | H | H | 3-Cl | —C(CH₃)₂—C(CH₃)=NOH | 203–205[1)] |
| 170 | F | F | H | H | 3-Cl | —C(CH₃)₂—C(CH₃)=NOCH₃ | 5.61 |
| 171 | F | F | H | H | 3-Cl | —C(CH₃)₂—C(CH₃)=NOC₂H₅ | 5.05 |

TABLE 1-continued

| 172 | F | F | H | H | 3-Cl | —C(CH₃)₂—C(CH₃)=NOC₃H₇-n | |
| 173 | H | Cl | H | H | 3-Cl | —C(CH₃)₂—CO—CH₃ | 5.02 |
| 174 | H | Cl | H | H | 3-Cl | —C(CH₃)₂—C(CH₃)=NOH | |
| 175 | H | Cl | H | H | 3-Cl | —C(CH₃)₂—C(CH₃)=NOCH₃ | 6.06 |
| 176 | H | Cl | H | H | 3-Cl | —C(CH₃)₂—C(CH₃)=NOC₂H₅ | 6.49 |
| 177 | H | Cl | H | H | 3-Cl | —C(CH₃)₂—C(CH₃)=NOC₃H₇-n | |
| 178 | F | F | H | H | H | —CH₂—C(3,4-Cl₂-C₆H₃)=NOC₂H₅ | |
| 179 | F | F | H | H | 3-Cl | —C(CH₃)₂—C(CH₃)=NOC₃H₇-n | |
| 180 | H | Cl | H | H | 3-Cl | —CH(CH₃)—C(CH₃)=NOC₃H₇-n | |
| 181 | Cl | F | H | H | H | —CH(CH₃)—C(CH₃)=NOC₃H₇-n | |
| 182 | H | Cl | H | H | H | —CH₂—C(CH₃)=NOC₃H₇-n | |
| 183 | H | Cl | H | H | H | —CH(CH₃)—C(CH₃)=NOC₃H₇-n | |
| 184 | F | F | H | H | H | —CH(CH₃)—C(CH₃)=NOC₃H₇-n | |
| 185 | F | Cl | H | H | H | —CH₂—C(CH₃)=NOC₃H₇-n | |
| 186 | F | F | H | H | H | —CH₂—C(CH₃)=NOC₃H₇-n | |
| 187 | F | F | H | H | H | —CH₂—C(cyclopropyl)=NOC₃H₇-n | |

TABLE 1-continued

| No. | | | | | | Structure | Data |
|---|---|---|---|---|---|---|---|
| 188 | F | F | H | H | H | —CH$_2$—C(=NOC$_3$H$_7$-n)—(1-Cl-cyclopropyl) | |
| 189 | F | F | H | H | H | —CH$_2$—C(=NOCH$_3$)—(3,4-di-CH$_3$-phenyl) | 5.58 (A-Isomer)*<br>5.29 (B-Isomer)* |
| 190 | F | F | H | H | H | —CH$_2$—C(=NOC$_2$H$_5$)—(3,4-di-CH$_3$-phenyl) | 5.94 (A-Isomer)<br>5.62 (B-Isomer)* |
| 191 | F | F | H | H | H | —CH$_2$—C(=NOCH$_3$)—(2,5-di-Cl-phenyl) | 5.62 (A-Isomer)*<br>5.44 (B-Isomer)* |
| 192 | F | F | H | H | H | —CH$_2$—C(=NOC$_2$H$_5$)—(2,5-di-Cl-phenyl) | 6.00 (A-Isomer)*<br>5.79 (B-Isomer)* |
| 193 | F | F | H | H | H | —CH$_2$—CO—(3-OCH$_3$-phenyl) | |
| 194 | F | F | H | H | H | —CH$_2$—C(=NOCH$_3$)—(3-OCH$_3$-phenyl) | |
| 195 | F | F | H | H | H | —CH$_2$—C(=NOC$_2$H$_5$)—(3-OCH$_3$-phenyl) | |
| 196 | F | F | H | H | H | —CH$_2$—CO—(3,4-di-Cl-phenyl) | |

TABLE 1-continued

| 197 | F | F | H | H | H | 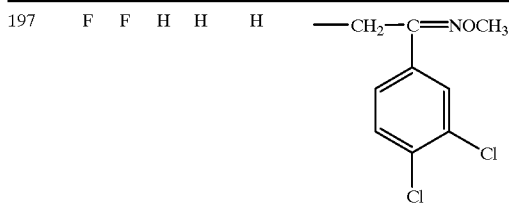 |

USE EXAMPLES

The compound of the formula (A)

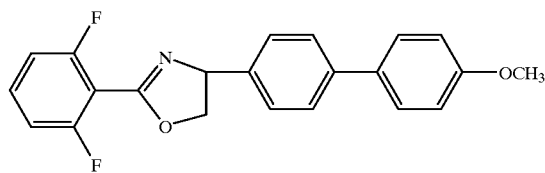

(A)

known from EP-A 0 432 661 was employed as the comparison substance in the following use examples.

Example A

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the desired time, the destruction in % is determined. 100% means that all the beetle larvae have been killed; 0% means that none of the beetle larvae have been killed.

In this test, for example, the compounds of Preparation Examples 1, 2, 4, 13, 14, 16, 20 and 21 caused a destruction of 100% after 7 days at an active compound concentration of, for example, 0.01%, while the known compound (A) showed no destruction.

Example B

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired time, the destruction in % is determined. 100% means that all the caterpillars have been killed; 0% means that none of the caterpillars have been killed.

In this test, for example, the compounds of Preparation Examples 2 and 4 caused a destruction of 100% after 7 days at an active compound concentration of, for example, 0.0001%, while the known compound (A) caused a destruction of only 5%.

Example C

Myzus Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier and the concentrate is diluted with water to the desired concentration.

Seedlings of broad beans (*Vicia faba*) infested by the green peach aphid (*Myzus persicae*) are dipped into the preparation of active compound of the desired concentration and placed in a plastic container.

After the desired time, the destruction in % is determined. 100% means that all the aphids have been killed; 0% means that none of the aphids has been killed.

In this test, for example, the compounds of Preparation Examples 4, 17 and 21 caused a destruction of 95% to 98% after 6 days at an active compound concentration of, for example, 0.01%, while the known compound (A) caused a destruction of only 5%.

Example D

*Spodoptera Frugiperda*-Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), as long as the leaves are still moist.

After the desired time, the destruction in % is determined. 100% means that all the caterpillars have been killed; 0% means that none of the caterpillars have been killed.

In this test, for example, the compounds of Preparation Examples 1, 2, 4, 10, 14, 16, 18, 20 and 21 caused a destruction of 100% after 7 days at an active compound concentration of, for example, 0.1%, while the known compound (A) showed no destruction.

Example E

Tetranychus Test (OP-resistant/dipping treatment)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are heavily infested with all stages of the two-spotted spider mite (*Tetranychus urticae*) are treated by being dipped into a preparation of the active compound of the desired concentration.

After the desired time, the effect in % is determined. 100% means that all the spider mites have been killed; 0% means that none of the spider mites have been killed.

In this test, for example, the compounds of Preparation Examples 1 and 2 caused a destruction of 98% after 13 days at an active compound concentration of, for example, 0.001%, while the known compound (A) showed a destruction of only 45%.

Example F

Test with Fly Larvae/Development-Inhibiting Action

Test animals: All larval stages of *Lucilia cuprina* (OP-resistant) [Pupae and adults (without contact with the active compound)]

Solvent: 35 parts by weight of ethylene glycol monomethyl ether

Emulsifier: 35 parts by weight of nonylphenol polyglycol ether

To produce a suitable formulation, three parts by weight of active compound are mixed with seven parts by weight of the abovementioned solvent/emulsifier mixture and the emulsion concentrate thus obtained is diluted with water to the particular desired concentration.

30–50 larvae per concentration are placed on horse meat (1 cm$^3$) in glass tubes, onto which 500 µl of the dilution to be tested are pipetted. The glass tubes are placed in a plastic beaker, the base of which is covered with sea sand, and are kept in a climatically controlled room (26° C.±1.5° C., 70% relative humidity ±10%). The action is monitored after 24 hours and 48 hours (larvicidal action). After the larvae have migrated (approx. 72 hours), the glass tubes are removed and perforated plastic lids are placed on the beakers. After 1½ times the duration of development (hatching of the control flies), the flies which have hatched and the pupae/pupal shells are counted.

The criterion for action is the occurrence of death in the treated larvae after 48 hours (larvicidal effect) or the inhibition of the hatching of adults from the pupae or the inhibition of puppation. The criterion for the in vitro action of a substance is the inhibition of flea development or a stop in development before the adult stage. 100% larvicidal action here means that all the larvae have died after 48 hours. 100% development-inhibiting action means that no adult flies have hatched.

In this test, for example, the compounds of Preparation Examples 4, 13, 15, 16, 17, 18, 20, 21, 23, 24, 25 and 26 caused a destruction of 100% at an active compound concentration of, for example, 1000 ppm.

What is claimed is:

1. Compounds of the formula (I)

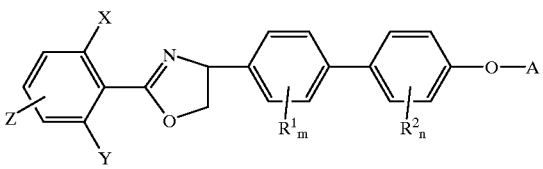

in which

X represents hydrogen, fluorine or chlorine,

Y represents fluorine, chlorine or methyl,

Z represents hydrogen, halogen, alkyl, alkoxy or dialkylamino, $R^1$ and $R^2$ independently of one another represent halogen, alkyl, alkoxy, alkylthio, halogenoalkyl, halogenoalkoxy or halogenoalkylthio, m and n independently of one another represent 0, 1 or 2 and A represents the grouping —$(CH_2)_p$—$(CR^3R^4)_q$—$(CH_2)_r$—R wherein $R^3$ and $R^4$ independently of one another represent hydrogen or alkyl, p, q and r independently of one another represent 0, 1, 2 or 3, at least one index being other than 0, and R represents cyano; or represents an optionally substituted, heterocyclic radical selected from

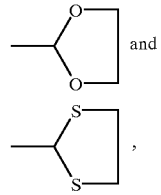

or represents one of the following groupings:

(a) —CO—$R^5$ (b) —CO—$OR^6$ (c) —CO—$NR^7R^8$ (d) —CS—$NR^7R^8$ (e) —C(=N—$R^{11}$)—$R^5$ (f) —C($R^5$)($OR^{12}$)($OR^{12}$)

-continued

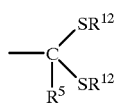 (g)

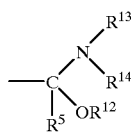 (h)

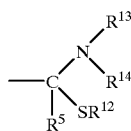 (i)

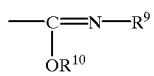 (j)

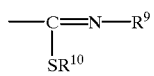 (k)

wherein
- $R^5$ represents hydrogen, alkyl, halogenoalkyl, optionally substituted cycloalkyl or optionally substituted aryl,
- $R^6$ represents alkyl, alkenyl, halogenoalkyl, halogenoalkenyl, optionally substituted arylalkyl or in each case optionally substituted cycloalkyl or cycloalkylalkyl,
- $R^7$ and $R^8$ independently of one another represent hydrogen, alkyl, alkoxy, alkenyl, halogenoalkyl, halogenoalkenyl, in each case optionally substituted aryl or arylalkyl, or in each case optionally substituted cycloalkyl or cycloalkylalkyl, or represent —$OR^6$ or —$NR^5R^6$, wherein
  - $R^5$ and $R^6$ have the above meaning, or
- $R^7$ and $R^8$ together represent a 5- or 6-membered alkylene chain, which optionally contains an oxygen atom,
- $R^9$ and $R^{10}$ independently of one another represent alkyl,
- $R^{11}$ represents —$OR^6$, —$NR^5R^6$ or —$N(R^5)$—$COOR^6$, wherein
  - $R^5$ and $R^6$ have the above meaning, and
- $R^{12}$, $R^{13}$ and $R^{14}$ independently of one another represent alkyl.

2. Compounds of the formula (I) according to claim 1, in which
- X represents hydrogen, fluorine or chlorine,
- Y represents fluorine, chlorine or methyl,
- Z represents hydrogen, fluorine, chlorine, $C_1$–$C_4$-alkyl, $C_1$–$C_4$-alkoxy or di($C_1$–$C_4$)alkylamino,
- $R^1$ and $R^2$ independently of one another represent fluorine, chlorine, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or $C_1$–$C_4$-halogenoalkylthio,
- m and n independently of one another represent 0, 1 or 2,
- A represents the grouping $(CH_2)_p$—$(CR^3R^4)_q$—$(CH_2)_r$—R, wherein
  - $R^3$ and $R^4$ independently of one another represent hydrogen or $C_1$–$C_4$-alkyl,
- p, q and r independently of one another represent 0, 1, 2 or 3, at least one index being other than 0 and the sum of the indices being not greater than 5,
- R represents cyano; or represents a heterocyclic radical selected from the group consisting of

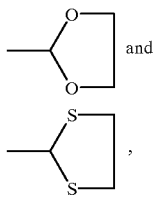 and 

and is optionally substituted by halogen, $C_1$–$C_4$-alkyl or $C_1$–$C_4$-halogenoalkyl, or represents one of the following groupings:

 (a)

 (b)

 (c)

 (d)

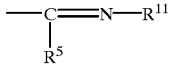 (e)

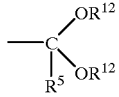 (f)

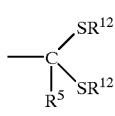 (g)

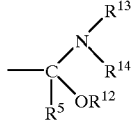 (h)

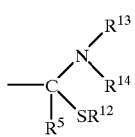 (i)

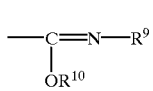 (j)

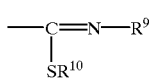 (k)

wherein
- $R^5$ represents hydrogen, $C_1$–$C_6$-alkyl, $C_1$–$C_4$-halogenoalkyl, or $C_3$–$C_6$-cycloalkyl which is optionally substituted once or several times in an identical or different manner by $C_1$–$C_4$-alkyl, halogen or $C_1$–$C_4$-halogenoalkyl, or represents phenyl which is optionally substituted once to five times in an identical or different manner by halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, di($C_1$–$C_4$)alkylamino, $C_1$–$C_4$-alkylcarbonylamino, $C_1$–$C_4$-alkylcarbonyl-$C_1$–$C_4$-alkylamino, cyano, nitro, —$COOR^{15}$ or —$CONR^{16}R^{17}$, $R^6$ represents $C_1$–$C_6$-alkyl, $C_1$–$C_6$-halogenoalkyl, $C_2$–$C_6$-alkenyl or $C_2$–$C_6$-halogenoalkenyl; or $C_3$–$C_6$-cycloalkyl or $C_3$–$C_6$-cycloalkyl-$C_1$–$C_4$-alkyl, in each case optionally substituted once or several times in an identical or different manner by $C_1$–$C_4$-alkyl, halogen or $C_1$–$C_4$-halogenoalkyl, or represents $C_6$–$C_{10}$-aryl-$C_1$–$C_6$-alkyl which is optionally substituted once to five times in an identical or different manner by halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, di($C_1$–$C_4$)alkylamino, cyano, nitro, —$COOR^{15}$ or —$CONR^{16}R^{17}$, $R^7$ and $R^8$ independently of one another represent hydrogen, $C_1$–$C_4$-alkyl, $C_1$–$C_4$-alkoxy, $C_1$–$C_4$-halogenoalkyl, $C_2$–$C_6$-alkenyl or $C_2$–$C_6$-halogenoalkenyl; or $C_3$–$C_6$-cycloalkyl or $C_3$–$C_6$-cycloalkyl-$C_1$–$C_4$-alkyl, in each case optionally substituted once or several times in an identical or different manner by $C_1$–$C_4$-alkyl, halogen or $C_1$–$C_4$-halogenoalkyl, or represent phenyl or phenyl-$C_1$–$C_4$-alkyl, in each case optionally substituted once to five times in an identical or different manner by halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, di($C_1$–$C_4$)alkylamino, cyano, nitro, —$COOR^{15}$ or —$CONR^{16}R^{17}$, or represent —$OR^6$ or —$NR^5R^6$, or $R^7$ and $R^8$ together represent —$(CH_2)_5$—, —$(CH_2)_6$— or —$(CH_2)_2$—O—$(CH_2)_2$—;

$R^9$ and $R^{10}$ independently of one another represent $C_1$–$C_4$-alkyl;

$R^{11}$ represents —$OR^6$—, —$NR^5R^6$ or —$N(R^5)$—$COOR^6$, and $R^{12}$, $R^{13}$ and $R^{14}$ independently of one another represent $C_1$–$C_4$-alkyl, $R^{15}$ represents hydrogen, $C_1$–$C_4$-alkyl or $C_1$–$C_4$-halogenoalkyl; or $C_3$–$C_6$-cycloalkyl which is optionally substituted once or several times in an identical or different manner by $C_1$–$C_4$-alkyl, halogen or $C_1$–$C_4$-halogenoalkyl, or represents phenyl which is optionally substituted once to five times in an identical or different manner by halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, di($C_1$–$C_4$)alkylamino, cyano, nitro, $C_1$–$C_6$-alkoxycarbonyl or di($C_1$–$C_6$)alkylaminocarbonyl, $R^{16}$ and $R^{17}$ independently of one another represent hydrogen, $C_1$–$C_4$-alkyl, $C_1$–$C_4$-alkoxy, $C_1$–$C_4$-halogenoalkyl, $C_2$–$C_6$-alkenyl or $C_2$–$C_6$-halogenoalkenyl; or $C_3$–$C_6$-cycloalkyl or $C_3$–$C_6$-cycloalkyl-$C_1$–$C_4$-alkyl, in each case optionally substituted once or several times in an identical or different manner by $C_1$–$C_4$-alkyl, halogen or $C_1$–$C_4$-halogenoalkyl, or represent phenyl or phenyl-$C_1$–$C_4$-alkyl, in each case optionally substituted once to five times in an identical or different manner by halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, di($C_1$–$C_4$)alkylamino, cyano, nitro, $C_1$–$C_6$-alkoxycarbonyl or di($C_1$–$C_6$)alkylaminocarbonyl, or represent —$OR^6$ or —$NR^5R^6$, or $R^{16}$ and $R^{17}$ together represent —$(CH_2)_5$—, —$(CH_2)_6$— or —$(CH_2)_2$—O—$(CH_2)_2$.

3. Compounds of the formula (I) according to claim 1, in which

X represents hydrogen, fluorine or chlorine,

Y represents fluorine or chlorine,

Z represents hydrogen, fluorine, chlorine, methyl, ethyl, methoxy, dimethylamino or diethylamino, $R^1$ and $R^2$ independently of one another represent fluorine, chlorine, methyl, ethyl, methoxy, methylthio, trifluoromethyl, trifluoromethoxy or trifluoromethylthio, m and n independently of one another represent 0, 1 or 2, A represents the grouping $(CH_2)_p$—$(CR^3R^4)_q$—$(CH_2)_r$—R, wherein $R^3$ and $R^4$ independently of one another represent hydrogen, methyl, ethyl, n- or i-propyl, n-, i-, s- or t-butyl;

p, q and r independently of one another represent 0, 1, 2 or 3, at least one index being other than 0, R represents cyano; or represents one of the following heterocyclic radicals

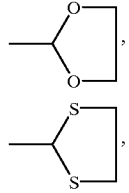

which are optionally substituted once to three times in an identical or different manner by fluorine, chlorine, bromine, methyl, ethyl, n- or i-propyl or trifluoromethyl;

or represents one of the following groupings:

(a)

(b)

(c)

(d)

(e)

(f)

-continued

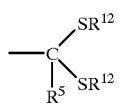 (g)

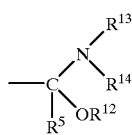 (h)

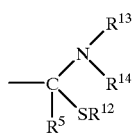 (i)

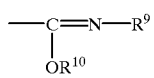 (j)

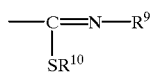 (k)

wherein $R^5$ represents hydrogen; methyl, ethyl, n- or i-propyl, the isomeric butyls, the isomeric pentyls or the isomeric hexyls; or $C_1$–$C_2$-halogenoalkyl having 1 to 5 identical or different halogen atoms, or cyclopropyl, cyclopentyl or cyclohexyl, in each case optionally substituted once to three times in an identical or different manner by fluorine, chlorine, methyl, ethyl, n- or i-propyl or $C_1$–$C_2$-halogenoalkyl having 1 to 5 identical or different halogen atoms, or represents phenyl which is optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, methylcarbonylamino, ethylcarbonylamino, methylcarbonyl-methylamino, cyano, nitro, —$COOR^{15}$ or —$CONR^{16}R^{17}$, $R^6$ represents methyl, ethyl, n- or i-propyl or n-, i-, s- or t-butyl; or $C_1$–$C_2$-halogenoalkyl having 1 to 5 identical or different halogen atoms, or allyl which is optionally substituted once or several times by fluorine and/or chlorine; or cyclopropyl, cyclopentyl, cyclohexyl, cyclopropyl-$C_1$–$C_2$-alkyl, cyclopentyl-$C_1$–$C_2$-alkyl or cyclohexyl-$C_1$–$C_2$-alkyl, in each case optionally substituted once to three times in an identical or different manner by fluorine, chlorine, methyl, ethyl, n- or i-propyl or $C_1$–$C_2$-halogenoalkyl having 1 to 5 identical or different halogen atoms, or represents phenyl-$C_1$–$C_2$-alkyl or naphthyl-$C_1$–$C_2$-alkyl, in each case optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, cyano, nitro, —$COOR^{15}$ or —$CONR^{16}R^{17}$, $R^7$ and $R^8$ independently of one another represent hydrogen, $C_1$–$C_4$-alkyl, methoxy, ethoxy or $C_1$–$C_3$-halogenoalkyl having 1 to 5 identical or different halogen atoms, or allyl which is optionally substituted once or several times by fluorine and/or chlorine; or cyclopropyl, cyclopentyl, cyclohexyl, cyclopropylmethyl, cyclopentylmethyl or cyclohexylmethyl, in each case optionally substituted once to three times in an identical or different manner by fluorine, chlorine, methyl, ethyl, n- or i-propyl or trifluoromethyl, or represent phenyl or phenyl-$C_1$–$C_2$-alkyl, in each case optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, cyano, nitro, —$COOR^{15}$ or —$CONR^{16}R^{17}$, or represent —$OR^6$ or —$NR^5R^6$, $R^9$ and $R^{10}$ independently of one another represent methyl, ethyl or n- or i-propyl;

$R^{11}$ represents —$OR^6$, —$NR^5R^6$ or —$N(R^5)$—$COOR^6$, and $R^{12}$, $R^{13}$ and $R^{14}$ independently of one another represent methyl, ethyl or n- or i-propyl, $R^{15}$ represents hydrogen, methyl, ethyl, or n- or i-propyl; or $C_1$–$C_2$-halogenoalkyl having 1 to 5 identical or different halogen atoms, or cyclopropyl, cyclopentyl or cyclohexyl, in each case optionally substituted once to three times in an identical or different manner by fluorine, chlorine, methyl, ethyl, n- or i-propyl or $C_1$–$C_2$-halogenoalkyl having 1 to 5 identical or different halogen atoms, or represents phenyl which is optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, cyano, nitro, $C_1$–$C_4$-alkoxycarbonyl or di($C_1$–$C_4$) alkylaminocarbonyl, $R^{16}$ and $R^{17}$ independently of one another represent hydrogen, $C_1$–$C_4$-alkyl, methoxy, ethoxy or $C_1$–$C_3$-halogenoalkyl having 1 to 5 identical or different halogen atoms, or allyl which is optionally substituted once or several times by fluorine and/or chlorine; or cyclopropyl, cyclopentyl, cyclohexyl, cyclopropylmethyl, cyclopentylmethyl or cyclohexylmethyl, in each case optionally substituted once to three times in an identical or different manner by fluorine, chlorine, methyl, ethyl, n- or i-propyl or trifluoromethyl, or represent phenyl or phenyl-$C_1$–$C_2$-alkyl, in each case optionally substituted once or twice in an identical or different manner by fluorine, chlorine, methyl, ethyl, methoxy, ethoxy, methylthio, trifluoromethyl, trifluoromethoxy, trifluoromethylthio, dimethylamino, diethylamino, cyano, nitro, $C_1$–$C_4$-alkoxycarbonyl or di($C_1$–$C_4$)alkylaminocarbonyl, or represent —$OR^6$ or —$NR^5R^6$.

4. A pesticidal composition comprising a pesticidally effective amount of at least one compound of the formula (I) according to claim 1 and an extender.

5. Method of controlling pests comprising applying to pests and/or their environment a pesticidally effective amount of at least one compound of the formula (I) according to claim 1.

6. A compound according to claim 1, which has the formula

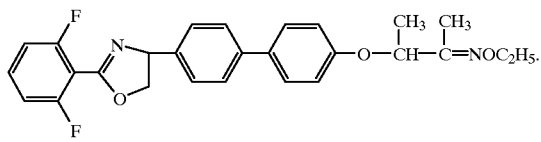

7. A compound according to claim 1, which has the formula

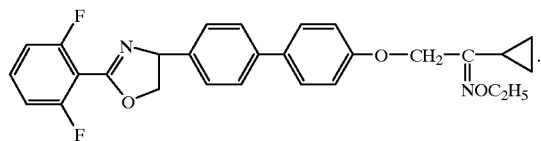

8. A compound according to claim 1, which has the formula

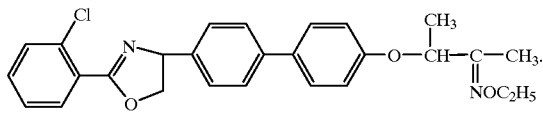

9. A compound according to claim 1, which has the formula

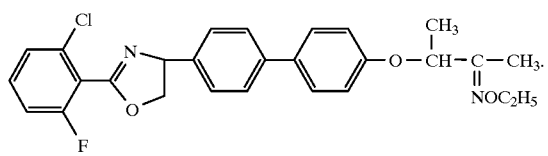

10. A compound according to claim 1, which has the formula

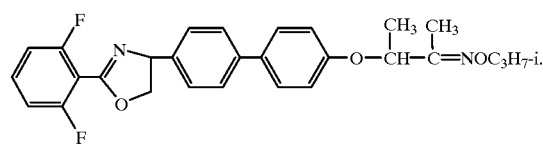

* * * * *